United States Patent
Kollarigowda et al.

(10) Patent No.: US 11,925,401 B1
(45) Date of Patent: Mar. 12, 2024

(54) METHOD OF CREATING BIOCOMPATIBLE POLYMERIC RESIN SYSTEMS FOR BONE REPAIR AND MANAGEMENT

(71) Applicant: MediCarbone, Inc., Tucson, AZ (US)

(72) Inventors: Ravichandran Kollarigowda, Tucson, AZ (US); Krishna Kolan, Tucson, AZ (US); Neda Saadatmanesh, Tucson, AZ (US); Hamid Saadatmanesh, Tucson, AZ (US); Abiraman Srinivasan, Tucson, AZ (US)

(73) Assignee: MEDICARBONE, INC., Tucson, AZ (US)

( * ) Notice: Subject to any disclaimer, the term of this patent is extended or adjusted under 35 U.S.C. 154(b) by 0 days.

(21) Appl. No.: 18/312,502

(22) Filed: May 4, 2023

Related U.S. Application Data

(60) Provisional application No. 63/374,337, filed on Sep. 1, 2022, provisional application No. 63/374,319, filed on Sep. 1, 2022.

(51) Int. Cl.
  *A61B 17/88* (2006.01)
  *A61L 27/12* (2006.01)
  *A61L 27/16* (2006.01)

(52) U.S. Cl.
  CPC .......... *A61B 17/8805* (2013.01); *A61L 27/12* (2013.01); *A61L 27/16* (2013.01)

(58) Field of Classification Search
  CPC ...................................................... A61L 27/16
  See application file for complete search history.

(56) References Cited

U.S. PATENT DOCUMENTS

| | | |
|---|---|---|
| 5,490,859 A | 2/1996 | Mische et al. |
| 6,066,167 A | 5/2000 | Lau et al. |
| 6,425,923 B1 | 6/2002 | Stalcup et al. |

(Continued)

FOREIGN PATENT DOCUMENTS

| | | | |
|---|---|---|---|
| WO | 2021123413 A1 | 6/2021 | |
| WO | WO-2021123413 A1 * | 6/2021 | ............. C04B 26/06 |

OTHER PUBLICATIONS

Wennergren et al. "Treatment and re-operation rates in one thousand and three hundred tibial fractures from the Swedish Fracture Register." European Journal of Orthopaedic Surgery & Traumatology 31 (2021): 143-154.

(Continued)

*Primary Examiner* — Michael F Pepitone
(74) *Attorney, Agent, or Firm* — NGUYEN TARBET LLC

(57) ABSTRACT

A photocurable device injection system for creating in situ polymerization via light or free-radical to enable fractured bone fixation. The system comprises a photosensitive polymeric resin sensitive to light, temperature, oxygen, enzymes, or a combination thereof. The photosensitive polymeric resin may be configured to cure at room temperature or physiological temperature with a light source. The photosensitive polymeric resin may be configured to depolymerize with ultrasonication, sonication, or a combination thereof. The system further comprises an implantable 3-dimensional biocompatible pouch comprising an optical light guide. The system further comprises one or more micro-sized ultrasonication probes configured to contact a three-dimensional pouch by one or more openings. The one or more probes may be configured to enable polymer outflow.

20 Claims, 5 Drawing Sheets

(56) References Cited

U.S. PATENT DOCUMENTS

| | | | |
|---|---|---|---|
| 7,008,446 | B1 | 3/2006 | Amis et al. |
| 7,806,900 | B2 | 10/2010 | Rabiner |
| 7,968,616 | B2 | 6/2011 | Meyer et al. |
| 8,747,412 | B2 | 6/2014 | Bae et al. |
| 10,292,823 | B2 | 5/2019 | Rabiner et al. |
| 10,426,641 | B2 | 10/2019 | Clerc et al. |
| 11,324,614 | B2 | 5/2022 | Trollsas et al. |
| 11,413,170 | B2 | 8/2022 | Pereira et al. |
| 2009/0299374 | A1 | 12/2009 | Tilson et al. |
| 2010/0076503 | A1 | 3/2010 | Beyar et al. |
| 2013/0023877 | A1 | 1/2013 | Rabiner et al. |
| 2013/0253661 | A1 | 9/2013 | D'Agostino et al. |
| 2014/0180288 | A1 | 6/2014 | DiPoto et al. |
| 2014/0207145 | A1 | 7/2014 | Sennett |
| 2014/0277568 | A1* | 9/2014 | Baehre ............... A61B 17/0401 424/423 |
| 2016/0015467 | A1* | 1/2016 | Vayser ................. G02B 1/048 600/245 |
| 2017/0239396 | A1 | 8/2017 | D'Agostino et al. |
| 2019/0117848 | A9 | 4/2019 | D'Agostino et al. |
| 2019/0357930 | A1* | 11/2019 | Cao ................. A61B 17/1659 |
| 2022/0361928 | A1 | 11/2022 | D'Agostino et al. |

OTHER PUBLICATIONS

Murphy et al. "3D bioprinting of stem cells and polymer/bioactive glass composite scaffolds for bone tissue engineering." International Journal of Bioprinting 3.1 (2017).

Kolan et al. "Bioprinting with bioactive glass loaded polylactic acid composite and human adipose stem cells." Bioprinting 18 (2020): e00075.

Bone Grafting—OMF—Grafton Bone Graft | Medtronic. https://www.medtronic.com/US-en/healthcare-professionals/products/spinal-orthopaedic/bone-grafting.html retrieved from web on Aug. 28, 2023.

DBM | Stryker. https://www.stryker.com/us/en/trauma-and-extremities/products/dbm.html retrieved from web on Aug. 28, 2023.

Hertz, Audrey, and Ian J. Bruce. "Inorganic materials for bone repair or replacement applications." (2007): 899-918.

Hench, Larry L. "The story of Bioglass®." Journal of Materials Science: Materials in Medicine 17.11 (2006): 967-978.

Kolken, H. Ma, and A. A. Zadpoor. "Auxetic mechanical metamaterials." RSC advances 7.9 (2017): 5111-5129.

Saxena, Krishna Kumar, Raj Das, and Emilio P. Calius. "Three decades of auxetics research—materials with negative Poisson's ratio: a review." Advanced Engineering Materials 18.11 (2016): 1847-1870.

Karageorgiou, Vassilis, and David Kaplan. "Porosity of 3D biomaterial scaffolds and osteogenesis." Biomaterials 26.27 (2005): 5474-5491.

North, Michael A., Chelsey A. Del Grosso, and Jonathan J. Wilker. "High strength underwater bonding with polymer mimics of mussel adhesive proteins." ACS applied materials & interfaces 9.8 (2017): 7866-7872.

Park et al. "A wireless pressure sensor integrated with a biodegradable polymer stent for biomedical applications." Sensors 16.6 (2016): 809.

Reeves, Jennifer A., Michael L. Allegrezza, and Dominik Konkolewicz. "Rise and fall: poly (phenyl vinyl ketone) photopolymerization and photodegradation under visible and UV radiation." Macromolecular rapid communications 38.13 (2017): 1600623.

Yang et al. "Synthesis and Characterization of Hydroxy-telechelic Four-arm Star-shaped Oligo (tetrahydrofuran), Their Crosslinking, and Thermomechanical Investigation of the Poymer Network." MRS Online Proceedings Library (OPL) 1403 (2012): mrsf11-1403.

Van Renterghem, Lieven M., Eric J. Goethals, and Filip E. Du Prez. "Star-shaped poly (tetrahydrofuran) with reactive end groups: Design, MALDI-TOF study, and solution behavior." Macromolecules 39.2 (2006): 528-534.

Caroli, Giuseppe, and Katja Loos. "Functional end groups in polytetrahydrofuran." Macromolecular Chemistry and Physics 214. 22 (2013): 2602-2606.

* cited by examiner

METHOD OF CREATING BIOCOMPATIBLE POLYMERIC RESIN SYSTEMS FOR BONE REPAIR AND MANAGEMENT

CROSS-REFERENCES TO RELATED APPLICATIONS

This application is a non-provisional and claims benefit of U.S. Provisional Application No. 63/374,337 filed Sep. 1, 2022, and U.S. Provisional Application No. 63/374,319 filed Sep. 1, 2022, the specifications of which are incorporated herein in their entirety by reference.

FIELD OF THE INVENTION

The present invention features methods for creating a polymeric resin system that is injectable, in situ curable, and removable via depolymerization/deplasticization from the anatomical location in a minimally invasive fashion if required after the surgical treatment. More specifically, the present invention relates to curable biocompatible polymeric resin systems with and without a light source for bone repair and management.

BACKGROUND OF THE INVENTION

Bone is a unique tissue that can repair itself after damage. However, some instances of damage, e.g., fractures or defects, require clinical intervention for proper alignment and healing. Currently, surgeons operate on patients with bone fractures using invasive procedures that can cause surgically-induced damage or iatrogenic injury. Thus, there is a need to create a simplified procedure for minimally invasive cement implantation and removal procedures.

The word fracture implies a broken bone. A bone may be completely or partially fractured. Fractures are commonly caused by trauma due to falls, motor vehicle accidents, or sports. Thinning of the bone due to osteoporosis in older adults can cause the bone to become fragile and break easily. Additionally, overuse injuries are a common cause of stress fractures in athletes.

There are four main types of fractures i) simple fractures, in which the fractured pieces of bone are well aligned and stable; ii) unstable fractures, in which fragments of the broken bone are misaligned and displaced; and iii) open (or compound) fractures, which are severe fractures in which the broken bones protrude through broken skin; this fracture is more prone to infection and requires immediate medical attention; and iv) greenstick fractures, which are a unique fracture most common in children that involves bending one side of the bone without any break in the other side of the bone. Almost all major bone fractures require some incision to allow for bone alignment and attachment of stabilizing rods, brackets, etc. Such incisions typically create significant trauma and require extensive rehabilitation time.

Additionally, certain diseases, disorders, and traumas that affect the skeletal system result in damage. The resulting damage, e.g., fractures or defects, in the skeletal system can lead to increased mortality, with the extent of the mortality link being different for different bones. The precise reason is unknown, but it is likely due to the associated comorbidities of fractures or defects. Fractures and defects can be the event that leads to the need for an implant, or the presence of an implant can also cause them. In addition, bone is the most transplanted tissue in the human body after blood. Therefore, careful consideration in designing orthopedic devices is essential to properly treat trauma in the skeletal system without harming the patient.

Orthopedic implants become necessary for fractures that need realignment and fixation for proper healing or in cases where the bone does not fully regenerate, producing bone defects. The design of these implants requires careful consideration of the material used, e.g., the biocompatibility, mechanical properties, and surface properties of the material, as well as its chemical and failure properties. Ideally, the material of the implant should have similar biomechanical properties to bone and also allow for integration with the native tissue while maintaining its integrity for the required duration. If the wrong material is chosen, the implants can lead to fractures, bone defects, or impairment of bone healing.

Current bone cements (i.e., implants; e.g., calcium phosphate bone cement) used during orthopedic implants have several limitations. For example, these bone cements require invasive implantation and extended fixation processes, which may require metal pins and screws, necessitating secondary surgeries upon removal. Additionally, during the implantation procedure, there is an increased risk of thermal necrosis as the use of bone cement can generate heat during the curing process. Therefore, new strategies are needed to avoid surgical revisions while maintaining or improving the fixation speed.

Thus, the present invention features minimally invasive approaches to implanting polymeric resin with the photosensitive material approach. The photosensitive polymeric resin can be implanted in a minimally invasive fashion by injecting the polymeric resin into the damaged site as a liquid form and curing it using an external energy source. Smart materials are implantable devices that provide therapeutic benefits and diagnostic capabilities. Integrating innovative implants into daily clinical practice has the potential to save massive costs for the healthcare system.

BRIEF SUMMARY OF THE INVENTION

It is an objective of the present invention to provide systems and methods that allow for in situ curing of a photocurable polymeric resin and removal of the cured polymer via depolymerization/deplasticization from the anatomical location in a minimally-invasive fashion, as specified in the independent claims. Embodiments of the invention are given in the dependent claims. Embodiments of the present invention can be freely combined if they are not mutually exclusive.

Orthopedic biomaterials must be highly biocompatible, non-toxic, and harmless to living tissue (e.g., the biomaterial must not cause adverse biological reactions). Unlike existing bone cement and stiff thermoplastic materials, the new resin system described herein matches the material properties and stiffness of surrounding bone tissue and exhibits low exothermic heat. Additionally, the cured polymer can be removed via end-chain depolymerization in situ using a light source, ultrasound, or thermally removed in a minimally invasive fashion.

Disclosed herein are light-responsive polymeric resin implants for bone stabilization systems. According to aspects illustrated herein, the present invention features a photocurable injection system that may include an intramedullary sleeve device with one or more access valves connected to devices (e.g., sensors) to detect and/or control the flow of the polymeric resin, a light-guide fiber configured to transmit light energy to the multilayer sleeve; and a photocurable polymeric resin comprising functional materials and a photoinitiator. In some embodiments, the photoinitiator is activated when the light-directing fiber transmits the light energy to initiate the polymerization of the photocurable polymeric resin into a cured polymer. The present invention may also further feature a multilayered sleeve/bag/balloon configured to control polymerization temperature, wherein the inner sleeve is sufficiently designed to pass the photocurable polymeric resin throughout the sleeve and wherein the sleeve is designed to guide the light guide fiber into the expandable portion of the sleeve.

The current disclosure also provides an improved method that does not use soluble or absorbable material and also resists infection. The present method includes inserting multilayer sleeves into the bone cavity and injecting a biocompatible polymeric resin. In this way, a solid peg is created inside the bone cavity that joins the sides of the fracture. The systems and methods described herein eliminate the need for open cuts and significantly reduce trauma and recovery time. In addition, the lack of metal eliminates potential interference problems with imaging techniques such as magnetic resonance imaging. The systems and methods described in this disclosure provide a non-absorbable solution for repairing and strengthening bones that can be left in place permanently or removed if desired.

In some embodiments, the present invention features a photocurable injection system for creating in-situ polymerization of a photocurable polymeric resin to enable fractured bone fixation and extraction of a cured polymer. In some embodiments, the system comprises a photocurable polymeric resin (e.g., a high stiffness polymeric resin) comprising function materials adapted to photocure into a cured polymer, a diffusive light guide tip, and a minimally invasive ultrasonic system for extracting the cured polymer. In some embodiments, the cured polymer is pulverizable. In some embodiments, the ultrasonic system is configured to pulverize the cured polymer into particles and extract said particles. In some embodiments, the functional materials are adapted to photocure into the cured polymer at a reaction temperature of at most 55 to 65° C. and a reaction temperature outside a sleeve device of at most 40° C. In some embodiments, the cured polymer shrinks in volume by less than 2% as compared to the original volume of the uncured polymer.

In some embodiments, the present invention also features a method for repairing a bone fracture (e.g., in a subject in need thereof). For example, the method may comprise a) injecting a photocurable polymeric resin (e.g., a high stiffness photocurable polymeric resin) into a medullary cavity of a fractured bone, the photocurable polymeric resin comprises functional materials that are adapted to photocure into the polymer, and the cured polymer is pulverizable, b) photopolymerizing the photocurable polymeric resin in-situ using a diffusive light guide tip to produce a cured polymer, the reaction temperature is at most 55 to 65° C. and outside a sleeve device the reaction temperature is at most additionally, the cured polymer shrinks in volume by less than 2% as compared to the original volume of the uncured polymer, c) pulverizing the cured polymer into particles using a minimally invasive ultrasonic system, and d) extracting the particles.

The current disclosure features a novel polymeric resin formulation that may comprise acrylates, low Tg-based modified polymers such alkenes (e.g., butadiene, polytetrafluoroethylene), derivatives of benzene (e.g., polystyrene, styrene), methacrylates (e.g., polymethyl methacrylate), polyamides (e.g., polyamide 6, polyamide 66), polysulfones (e.g., polyethersulfone), sulfides (e.g., polyphenylene sulfide), nitriles (e.g., acrylonitrile, polyacrylonitrile), phthalates (e.g., polypropylene terephthalate, polyethylene terephthalate), polyacetal, polycarbonate, polyurethane, polyamide-imide, polylactic acid, ethylene-vinyl acetate, polyfluoro vinylidene.

The present disclosure is not limited to a particular material or configuration of carbon or another bag or sleeves or balloons. The curing system is not limited to a UV light source and may include visible light, temperature, oxygen, and in some cases, can activate with free radicals and enzymes or other appropriate mechanisms.

The selection of the polymeric resin formulation, sleeves, and curing process can be adapted with machine learning with artificial intelligence (AI). The selection of each of the components in the system can be simplified by considering different factors such as patient age, bone density, region of fracture, and classification of fracture. AI can help detect the formulation of polymeric resin and the curing process with the preprogrammed machine learning system.

The intramedullary device is designed to provide for sleeve insertion, curing, and removal using a minimally invasive approach. The present invention incorporates consideration of, among other things, the anatomy of the host tissue where the sleeve/resins are implanted, the load-distributing properties of the cured polymer, and implant systems of the present invention, ideally achieving natural bone-like properties. The properties of the polymeric resin and corresponding cured polymer (e.g., the implant) may match the qualities of the natural bone, including factors influenced by the age and sex of the patient. Additionally, implants may be customized to the local macro and micro physiological environment.

One of the unique and inventive technical features of the present invention is the use of functional materials within the photocurable polymeric resin. Without wishing to limit the invention to any theory or mechanism, it is believed that the technical feature of the present invention advantageously provides for a polymeric resin that can be cured at a reaction temperature of less than 65° C. The resulting cured polymer also shrinks in volume by less than 2% as compared to the original volume of the uncured polymer. Lastly, the functional materials with the photocurable polymeric resin allows the cured polymer to be pulverizable, which aids in the removal of the cured polymer. None of the presently known prior references or work has the unique inventive technical feature of the present invention.

Furthermore, the prior references teach away from the present invention. For example, current ultrasound systems used to remove cured bone cement are adapted to melt or soften the bone cement for its removal. The use of specific functional materials allows the bone cement (e.g., the cured polymer) of the present invention to be pulverized into particles using the ultrasonic system described herein.

Additionally, current bone stabilization systems may utilize degradable materials, which may eliminate the need for surgical implant removal and thus avoid the complications associated with surgeries for implant removal. However, although there are currently degradable polymer fixation devices on the market, they are only applied to non-load-bearing craniofacial applications. Furthermore, these degradable polymeric fixation devices are not ideal options for load-bearing fixation, as they would need to be made much thicker to have the required strength for load-bearing applications.

Lastly, current commercial bone cement can have up to 21% volumetric shrinkage. Contrastingly, the bone cement of the present invention shrinks by less than 2%.

The current invention offers solutions to fix orthopedic fractures using minimally invasive techniques that can be custom designed for the patient's requirements. A significant innovation of the present technology is the minimally invasive surgical insertion of sleeves and resin implants which can be cured with UV-Visible light or without UV-Visible light sources by following a free-radical polymerization approach and removal of the implant after fracture healing. The present invention offers solutions for civilian and combat orthopedic trauma and can also be used for other bone disease conditions and veterinary orthopedic fracture fixation.

Any feature or combination of features described herein are included within the scope of the present invention provided that the features included in any such combination are not mutually inconsistent as will be apparent from the context, this specification, and the knowledge of one of ordinary skills in the art. Additional advantages and aspects of the present invention are apparent in the following detailed description and claims.

BRIEF DESCRIPTION OF THE SEVERAL
VIEWS OF THE DRAWING(S)

The features and advantages of the present invention will become apparent from a consideration of the following detailed description presented in connection with the accompanying drawings in which:

FIG. 1A shows a proximal and distal end embodiment of the present invention's flexible light guide and flexible injectable sleeve insertion. The IM device of the present invention is a light guide with the port device mounted at a distal end of the flexible insertion sleeves. The injecting polymeric resin system is connected to the flexible insertion of the sleeve.

FIG. 1B shows a proximal and distal end embodiment of the present invention's flexible light guide and injectable sleeve insertion. The IM device of the present invention is a coil structure set up with a light guide with the port, which goes around the sleeve device mounted at a distal end of the flexible insertion sleeves injecting a polymeric resin system connected to the flexible insertion of the sleeve.

Figure 1A:
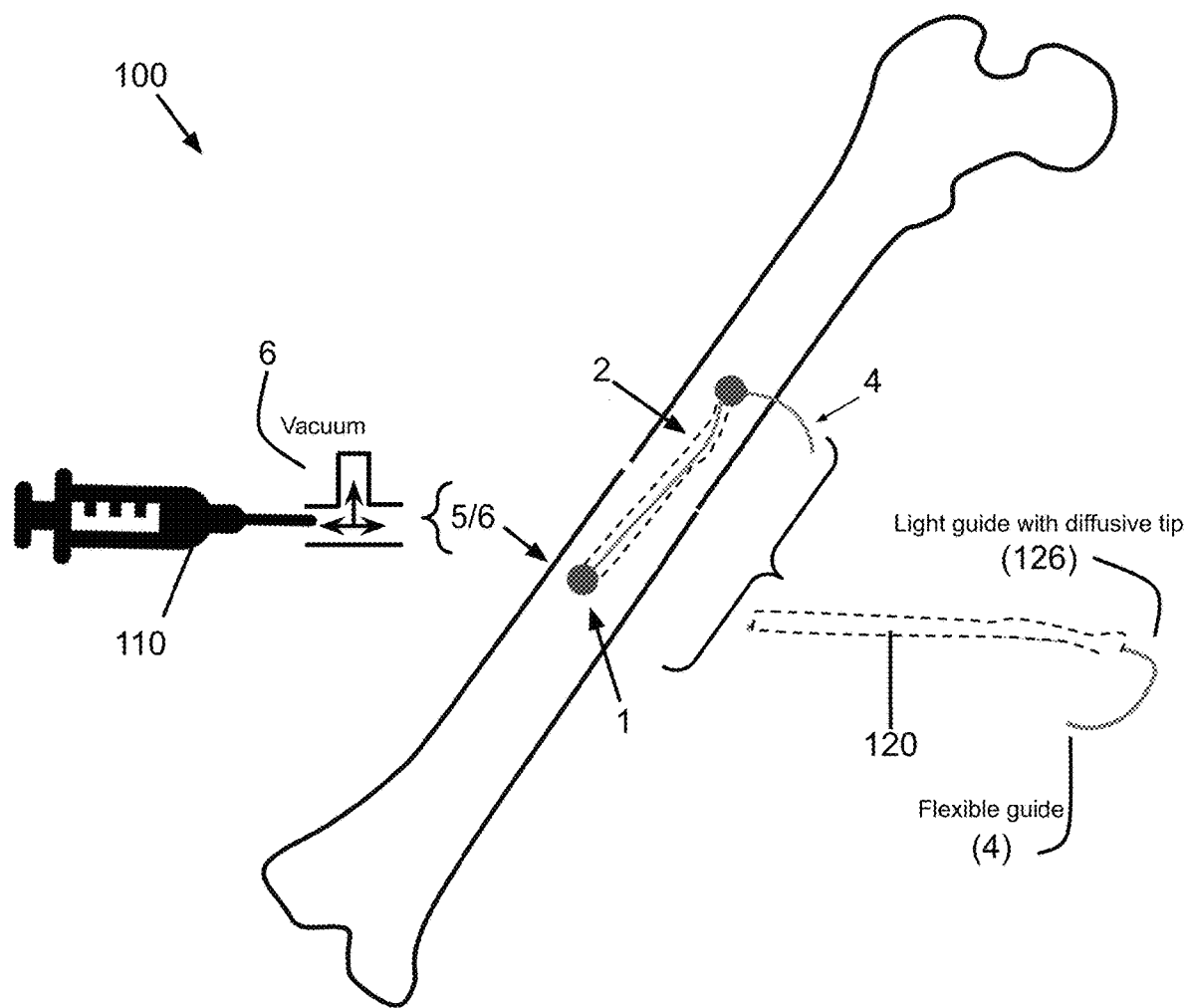
FIG. 1C shows a proximal end embodiment of the present invention's flexible light guide and flexible injectable sleeve insertion. The IM device of the present invention is a light guide with an injecting polymeric resin system connected to the flexible insertion of the sleeve.
FIG. 1D shows an embodiment of the present invention featuring customized ultrasonic probe setups for removing cured polymeric resin systems with different structures, which can easily be used to remove material in a minimally invasive fashion from the teeth, bones, or any other implantable application.

DETAILED DESCRIPTION OF THE
INVENTION

Following is a list of elements corresponding to a particular element referred to herein:
1 sleeve proximal end
2 intramedullary (IM) sleeve system
3 first light guide
4 flexible light guide
5 proximal end access valve
6 access valve
100 system
110 resin
120 sleeve/bag/balloon/tube/fabric
122 opening
124 access port
126 optical guide/light guide with diffusive tip
130 probes Terms Unless otherwise explained, all technical and scientific terms used herein have the same meaning as commonly understood by one of ordinary skills in the art to which a disclosed invention belongs. The singular terms "a," "an," and "the" include plural referents unless context clearly indicates otherwise. Similarly, the word "or" is intended to include "and" unless the context clearly indicates otherwise. The term "comprising" means that other elements can also be present in addition to the defined elements presented. The use of "comprising" indicates inclusion rather than limitation. Stated another way, the term "comprising" means "including principally, but not necessary solely." Furthermore, variations of the word "comprising," such as "comprise" and "comprises," have correspondingly the same meanings. In one respect, the technology described herein is related to the described compositions, methods, and respective component(s) thereof, as essential to the invention, yet open to the inclusion of unspecified elements, essential or not ("comprising").

Although methods and materials similar or equivalent to those described herein can be used to practice or test the disclosed technology, suitable methods and materials are described below. The materials, methods, and examples are illustrative only and not intended to be limiting.

A "subject" is an individual and includes, but is not limited to, a mammal (e.g., a human, horse, pig, rabbit, dog, sheep, goat, non-human primate, cow, cat, guinea pig, or rodent), a fish, a bird, a reptile or an amphibian. The term does not denote a particular age or sex. Thus, adult and newborn subjects, as well as fetuses, whether male or female, are intended to be included. A "patient" is a subject afflicted with a disease or disorder. The term "patient" includes human and veterinary subjects.

As used herein, "high stiffness" refers to a stiff that is similar to or equals that of a load bearing bone. For example, high stiffness, as used herein, may refer to stiffness ranging from 0.5 GPa up to 15 GPa.

As used herein, a "low melting point" refers to materials with melting points of at most 100° C.

The present invention addresses the shortcomings in existing technologies and introduces a polymeric resin that is implantable and depolymerizable in a minimally invasive fashion. The present invention features a novel, formulated photocurable polymeric resin comprising functional materials (e.g., low melting point acrylate-based prepolymers). The polymeric resin's structural properties are influenced when the functional materials are covalently bonded. When an ultrasonic probe meets the cement, the cement begins to break up into chunks/particles, and vacuum suction removes the chunks/particles of the cured polymer. Because the entire removal process can be performed inside a sleeve device, the probability of missing chunks/particles of the cured polymer is greatly reduced as these chunks/particles will be trapped in the sleeve and removed upon removal of the sleeve. Moreover, the functional materials also help to improve the mechanical properties of the cured polymer or cement. The functional materials also help to melt the cured polymer with minimal temperature release, whereas existing bone cement releases more heat during the melting of the bone cement. The present invention's polymeric resin comprising functional materials can be cured with a light source and also can follow a traditional free-radical curing process that enables the removal of polymer-based implants in orthopedic, dental, or other applications in a minimally invasive way.

For purposes of summarizing the disclosure, certain aspects, advantages, and novel features of the disclosure are described herein. It is to be understood that not necessarily all such advantages may be achieved in accordance with any particular embodiments of the disclosure. Thus, the disclosure may be embodied or carried out in a manner that achieves or optimizes one advantage or group of advantages as taught herein without necessarily achieving other advantages as may be taught or suggested herein.

Additionally, although embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. Moreover, while a number of variations have been shown and described in varying detail, other modifications, which are within the scope of the present disclosure, will be readily apparent to those of skill in the art based upon this disclosure. It is also contemplated that various combinations or sub-combinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described herein.

Referring now to FIGS. 1A-2E, the present invention features a photocurable injection system (100) for creating in-situ polymerization of a photocurable polymeric resin to enable fractured bone fixation and extraction of a cured polymer. The system may comprise a) a photocurable polymeric resin (110) comprising function materials that are adapted to photocure into the cured polymer, b) a diffusive light guide tip, and c) a minimally invasive ultrasonic system for extracting the cured polymer (e.g., through a laparoscopic opening).

In some embodiments, the photocurable injection system (100) comprises a) photocurable polymeric resin (110, e.g., a high stiffness photocurable polymeric resin) comprising functional materials that are adapted to photocure into the cured polymer, b) a diffusive light guide tip, and c) a minimally invasive ultrasonic system for extracting the cured polymer. In some embodiments, the cured polymer is pulverizable. In some embodiments, the ultrasonic system is configured to pulverize the cured polymer into particles and is configured to extract the particles. In some embodiments, the ultrasonic system is configured to extract particles through a laparoscopic opening.

In some embodiments, the photocurable injection system (100) comprises a) photocurable polymeric resin (110, e.g., a high stiffness photocurable polymeric resin) comprising functional materials that are adapted to photocure into the cured polymer at a reaction temperature of at most 55 to 65° C., b) a diffusive light guide tip, and c) a minimally invasive ultrasonic system for extracting the cured polymer (e.g., through a laparoscopic opening).

The photocurable injection systems (100) described herein may further comprise a sleeve device. In some embodiments, the photocurable polymeric resin (110) is photocured into the polymer inside the sleeve device. In some embodiments, when curing the photocurable polymeric resin (110) into the polymer inside the sleeve device, the temperature outside the sleeve is at most 40° C.

In some embodiments, the photocurable injection system (100) comprises a) photocurable polymeric resin (110, e.g., a high stiffness photocurable polymeric resin) comprising functional materials that are adapted to photocure into the cured polymer, b) a diffusive light guide tip, and c) a minimally invasive ultrasonic system for extracting the cured polymer (e.g., through a laparoscopic opening). In some embodiments, the cured polymer shrinks in volume by less than 2% as compared to the original volume of the uncured polymer.

In some embodiments, at least some or all of the components in the system (100), e.g., the polymeric resin/cured polymer, the sleeve device, the sensors, and/or cameras, further comprise antibiotics or antibiotic drugs. For example, antibiotic drugs may be added to the outer surface of the components used in the system (100). In other embodiments, at least some or all of the components in the system (100), e.g., the polymeric resin/cured polymer, the sleeve device, the sensors, and/or cameras, further comprise proteins (e.g., bone morphogenic protein or other growth factors) added to the outer surface of the components. For example, an infection may develop in a patient after a minimally invasive surgical procedure, requiring the patient to undergo antibiotic treatment. An antibiotic drug may be added to the outer surface of the expandable portion of the sleeve device to prevent and/or combat a possible infection. Additionally, proteins, such as, for example, bone morphogenic protein or other growth factors, have been shown to induce the formation of cartilage and bone. Therefore, a protein, e.g., a growth factor may be added to the outer surface of the sleeves to help influence the formation of new bone.

Polymeric Resin/Polymer

The present invention may feature a biocompatible polymer produced by curing a photocurable composition. In some embodiments, the photocurable composition comprises: a) a photocurable polymeric resin (110); b) functional materials, wherein the functional materials comprise a monomer, one or more comonomers, a crosslinker (e.g., a short chain cross-linker, a long-chain crosslinker, or a combination thereof), or a combination thereof; and c) a photoinitiator. In some embodiments, the functional materials are adapted to photocure the reactive mixture into the polymer composition (e.g., a stiff polymer composition).

In some embodiments, the photocurable composition comprises about 80% to 75% W/W or V/V of a polymeric resin (110), about 15% to 5% W/W or V/V of isobornyl methacrylate, about 10% to 1% W/W or V/V of diurethane dimethacrylate, about 5% to W/W or V/V of ethylene glycol dimethacrylate, about 5% to 0.1% W/W or V/V of polycaprolactone dimethacrylate; and about 2 to 0.1% W/W or V/V of a photoinitiator.

In some embodiments, the polymeric resin is sensitive to light, temperature, oxygen, enzymes, or a combination thereof. The polymeric resin may be configured to cure at room temperature or at a physiological temperature with a light source. In some embodiments, the polymeric resin is a photocurable polymeric resin. The removal or extraction of cured photocurable polymeric resin (110) can occur at room temperature or physiological temperature or at a temperature lower than 65° C. with ultrasonication, sonication, or a combination thereof.

In some embodiments, the system (100) may comprise a stiff (e.g., a high stiffness) polymer, e.g., the stiffness of the polymer described herein is similar to or equal to the stiffness of a load bearing bone. In some embodiments, the stiffness of the cured polymer is about 0.5 GPa to about 15 GPa. In some embodiments, the stiffness of the cured polymer is about 0.5 GPa to 1.0 GPa, or about 0.5 GPa to 5.0 GPa, or about 0.5 GPa to 10 GPa, or about 0.5 GPa to 15 GPa, or about 1.0 GPa to 5.0 GPa, or about 1.0 GPa to 10 GPa, or about 1.0 GPa to 15 GPa, or about 5.0 GPa to 10 GPa, or about 5.0 GPa to 15 GPa, or about 10 GPa to 15 GPa. In some embodiments, the stiffness of the cured polymer is about 0.5 GPa, about 1.0 GPa, about 5.0 GPa, about 10 GPa, or about GPa.

In some embodiments, the cured polymer is pulverizable. In some embodiments, an ultrasonic system, e.g., the ultrasonic system described herein, is configured to pulverize the cured polymer into particles. The ultrasonic system may also be configured to extract said particle.

In some embodiments, the functional materials are adapted to photocure into the cured polymer at room temperature (e.g., at most 20° C.) or at physiological temperature (e.g., at most 40° C.). In other embodiments, the functional materials are adapted to photocure into the cured polymer at a reaction temperature of 55 to 65° C. In some embodiments, the reaction temperature to photocure the polymeric resin is about 20° C. to 65° C., or about 20° C. to 60° C., or about 20° C. to 55° C., or about 20° C. to 50° C., or about 20° C. to 45° C., or about 20° C. to 40° C., or about 20° C. to 35° C., or about 20° C. to 30° C., or about 20° C. to 25° C., or about 25° C. to 65° C., or about 25° C. to 60° C., or about 25° C. to 55° C., or about 25° C. to 50° C., or about 25° C. to 45° C., or about 25° C. to 40° C., or about 25° C. to 35° C., or about 25° C. to 30° C. In some embodiments, the reaction temperature to photocure the polymeric resin is about 30° C. to 65° C., or about 30° C. to 60° C., or about 30° C. to 55° C., or about 30° C. to 50° C., or about 30° C. to 45° C., or about 30° C. to 40° C., or about 30° C. to 35° C., or about 35° C. to 65° C., or about 35° C. to 60° C., or about 35° C. to 55° C., or about 35° C. to 50° C., or about 35° C. to 45° C., or about 35° C. to 40° C. In some embodiments, the reaction temperature to photocure the polymeric resin is about 40° C. to 65° C., or about 40° C. to 60° C., or about 40° C. to 55° C., or about 40° C. to 45° C., or about 45° C. to 65° C., or about 45° C. to 60° C., or about 45° C. to 55° C., or about 45° C. to 50° C., or about 50° C. to 65° C., or about 50° C. to 55° C., or about 55° C. to 60° C. In some embodiments, the functional materials are adapted to photocure into the cured polymer at a reaction temperature of about 20° C., or about 25° C., or about 30° C., or about 35° C., 40° C., or about 45° C. or about 50° C., or about 55° C., or about 60° C., or about 65° C.

In some embodiments, the reaction temperature outside a sleeve device is at most 40° C. In some embodiments, the reaction temperature outside a sleeve device is at most 39° C. In some embodiments, the reaction temperature outside a sleeve device is at most 38° C. In some embodiments, the reaction temperature outside a sleeve device is at most 37° C. In some embodiments, the reaction temperature outside a sleeve device is at most 36° C. In some embodiments, the reaction temperature outside a sleeve device is at most 35° C.

In some embodiments, the cured polymer shrinks in volume by less than 2% as compared to the original volume of the uncured polymer. In some embodiments, the cured polymer shrinks in volume by less than 1% as compared to the original volume of the uncured polymer. In some embodiments, the cured polymer shrinks in volume by less than 3% as compared to the original volume of the uncured polymer. In some embodiments, the cured polymer shrinks in volume by less than 4% as compared to the original volume of the uncured polymer. In some embodiments, the cured polymer shrinks in volume by less than 5% as compared to the original volume of the uncured polymer. In some embodiments, the cured polymer shrinks in volume by less than 8% as compared to the original volume of the uncured polymer. In some embodiments, the cured polymer shrinks in volume by less than 10% as compared to the original volume of the uncured polymer.

The functional materials described herein may comprise a monomer, one or more comonomers, a short-chain cross-linker, a long-chain cross-linker, and a photoinitiator. In some embodiments, the functional materials described herein may act as a monomer, comonomers, short-chain cross-linkers, long-chain cross-linkers, or a combination thereof.

In some embodiments, the photocurable polymeric resin (110) further comprises a photoinitiator. In some embodiments, the photoinitiator comprises a free radical photoinitiator, a cationic-based photoinitiator, or a combination thereof. In some embodiments, the photocurable polymeric resin (110) comprises function materials that are adapted to photocure into the cured polymer upon activation by the photoinitiator (e.g., a free-radical or a cationic-based photoinitiator or combination thereof). Non-limiting examples of photoinitiators that may be used in accordance with the present invention include, but are not limited to, diphenyl (2,4,6-trimethylbenzoyl) phosphine oxide, phenylbis(2,4,6-trimethylbenzoyl)phosphine oxide, 2-Hydroxy-4'-(2-hydroxyethoxy)-2-methylpropiophenone, Ethyl Phenyl(2,4,6-trimethylbenzoyl)phosphinate, 2,2'-Azobis(2-methylpropionitrile), 2-Benzyl-2-(dimethylamino)-4'-morpholinobutyrophenone, 2-Dimethylamino-2-(4-methylbenzyl)-1-(4-morpholin-4-yl-phenyl)-butan-1-one, Benzoyl Peroxide, Camphorquinone, 2-Isopropylthioxanthone, 4-Benzoylbiphenyl, 2,4-Diethyl-9H-thioxanthen-9-one, 1-Chloro-4-propoxy-9H-thioxanthen-9-one, 4,4'-Bis(diethylamino)benzophenone, 4,4'-Bis(dimethylamino)benzophenone2-Chlorothioxanthen-9-one, 4-(Dimethylamino)benzophenone, 3'-Hydroxyacetophenone, methybenzoylformate, phenanthrenequinone, thioxanthen-9-one, camphorquinone, 2-Hydroxy-4'-(2-hydroxyethoxy)-2-methylpropiophenone, or a combination thereof.

In some embodiments, the polymeric resin (110; e.g., the photosensitive polymeric resin) comprises about 0.1 to 10% W/W or V/V of the photoinitiator. In some embodiments, the polymeric resin (110; e.g., the photosensitive polymeric resin) comprises about 0.1 to 5% W/W or V/V of the photoinitiator. In some embodiments, the polymeric resin (110; e.g., the photosensitive polymeric resin) comprises about 0.1 to 2% W/W or V/V of the photoinitiator.

In other embodiments, the polymeric resin (110; e.g., the photosensitive polymeric resin) may comprise about 0.1 to 10%, or about 0.1 to 9%, or about 0.1 to 8%, or about 0.1 to 7%, or about 0.1 to 6%, or about 0.1 to 5%, or about 0.1 to 4%, or about to 3%, or about 0.1 to 2%, or about 0.1 to 1%, or about 0.1 to 0.5%, or about 0.5 to 10%, or about 0.5 to 9%, or about 0.5 to 8%, or about 0.5 to 7%, or about 0.5 to 6%, or about 0.5 to 5%, or about 0.5 to 4%, or about 0.5 to 3%, or about 0.5 to 2%, or about 0.5 to 1% W/W or V/V of the photoinitiator. In some embodiments, the polymeric resin (110; e.g., the photosensitive polymeric resin) may comprise about 1 to 10%, or about 1 to 9%, or about 1 to 8%, or about 1 to 7%, or about 1 to 6%, or about 1 to 5%, or about 1 to 4%, or about 1 to 3%, or about 1 to 2%, or about 2 to 10%, or about 2 to 9%, or about 2 to 8%, or about 2 to 7%, or about 2 to 6%, or about 2 to 5%, or about 2 to 4%, or about 2 to 3% or about 3 to 10%, or about 3 to 9%, or about 3 to 8%, or about 3 to 7%, or about 3 to 6%, or about 3 to 5%, or about 3 to 4% W/W or V/V of the photoinitiator. In some embodiments, the polymeric resin (110; e.g., the photosensitive polymeric resin) may comprise about 4 to 10%, or about 4 to 9%, or about 4 to 8%, or about 4 to 7%, or about 4 to 6%, or about 4 to 5%, or about 5 to 10%, or about 5 to 9%, or about 5 to 8%, or about 5 to 7%, or about 5 to 6%, or about 6 to 10%, or about 6 to 9%, or about 6 to 8%, or about 6 to 7%, or about 7 to 10%, or about 7 to 9%, or about 7 to 8%, or about 8 to 10%, or about 8 to 9%, or about 9 to 10% W/W or V/V of the photoinitiator.

In some embodiments, the polymeric resin (110; e.g., the photosensitive polymeric resin) may comprise about 0.1% W/W or V/V of the photoinitiator. In some embodiments, the polymeric resin (110; e.g., the photosensitive polymeric resin) may comprise about 0.5% W/W or V/V of the photoinitiator. In some embodiments, the polymeric resin (110; e.g., the photosensitive polymeric resin) may comprise about 1% W/W or V/V of the photoinitiator. In some embodiments, the polymeric resin (110; e.g., the photosensitive polymeric resin) may comprise about 2% W/W or V/V of the photoinitiator. In some embodiments, the polymeric resin (110; e.g., the photosensitive polymeric resin) may comprise about 3% W/W or V/V of the photoinitiator. In some embodiments, the polymeric resin (110; e.g., the photosensitive polymeric resin) may comprise about 4% W/W or V/V of the photoinitiator. In some embodiments, the polymeric resin (110; e.g., the photosensitive polymeric resin) may comprise about 5% W/W or V/V of the photoinitiator. In some embodiments, the polymeric resin (110; e.g., the photosensitive polymeric resin) may comprise about 6% W/W or V/V of the photoinitiator. In some embodiments, the polymeric resin (110; e.g., the photosensitive polymeric resin) may comprise about 7% W/W or V/V of the photoinitiator. In some embodiments, the polymeric resin (110; e.g., the photosensitive polymeric resin) may comprise about 8% W/W or V/V of the photoinitiator. In some embodiments, the polymeric resin (110; e.g., the photosensitive polymeric resin) may comprise about 9% W/W or V/V of the photoinitiator. In some embodiments, the polymeric resin (110; e.g., the photosensitive polymeric resin) may comprise about 10% W/W or V/V of the photoinitiator.

In some embodiments, the polymeric resin (110; e.g., the photosensitive polymeric resin) may comprise functional materials. In some embodiments, the functional materials may comprise acrylate compounds, methacrylate compounds, or a combination thereof. In some embodiments, the functional material may comprise acrylate/methacrylate compounds (or polymeric resins) crosslinked with low melting point materials. In some embodiments, the functional material may comprise methacrylic acid.

In some embodiments, the functional material comprises comprise low melting point (e.g., at most 100° C.) polymers modified with acrylate or methacrylate functional groups, a thermoplastic polymer with acrylate or methacrylate functional groups, semicrystalline polymers, unsaturated fatty acids modified with acrylate or methacrylate functional groups, modified acrylate or methacrylate functional groups of polypeptides, dendrimers, natural polysaccharide-based units, materials that can crosslink or act as comonomers or monomers with a photosensitive functional materials polymeric resin, or a combination thereof.

Non-limiting examples of acrylate compounds include but are not limited to butyl acrylate, n-propyl acrylate, iso-Decyl acrylate, n-hexyl acrylate, sec-butyl acrylate, or 2-methoxyethyl acrylate. Non-limiting example of methacrylate compounds include but are not limited to methyl methacrylate, 2-hydroxyethyl methacrylate, n-decyl methacrylate, 3,3,5-Trimethylcyclohexyl methacrylate, n-propyl methacrylate, benzyl methacrylate, isobutyryl methacrylate, polycaprolactone methacrylate, N-butyl-methacrylate, n-octyl methacrylate, phenyl methacrylate, sec-butyl methacrylate, iso-butyl methacrylate, cyclohexyl methacrylate, 2-phenoxyethyl methacrylate, diurethane methacrylate, ethyl methacrylate, 2-hydroxyethyl methacrylate, 2-ethylhexyl methacrylate, or 2-n-butoxyethyl methacrylate.

In some embodiments, the functional material may comprise materials modified with methacrylate or acrylate chemistry such as styrene. In some embodiments, the functional material may comprise ethylene glycol-based dimethacrylates such as bisphenol a dimethacrylate, 1,3-butanediol dimethacrylate, poly(ethylene glycol) dimethacrylate, triethylene glycol dimethacrylate, ethylene glycol dimethacrylate, Di(ethylene glycol) dimethacrylate polycaprolactone dimethacrylate, 1,10-decanediol dimethacrylate diurethane dimethacrylate, glycerol dimethacrylate fluorescein o,o'-dimethacrylate.

In some embodiments, the polymeric resin (110) comprises functional materials selected from the group comprising polyesters, modified polyesters, urethanes, modified urethanes, thermoplastics, polypeptides, and modified polysaccharides. In some embodiments, the polymeric resin (110) may be sensitive to temperature such that the resin is activated thermally near the Tg of the polymer. In some embodiments, the resin (110) may be sensitive to oxygen, such that the resin, in the presence of oxygen, is known to inhibit radical polymerization by reacting with the active radicals and generating dead chain ends.

In some embodiments, the functional materials comprise a resin solution, a comonomer, one or more crosslinkers (e.g., a short chain crosslinker, a long chain crosslinker, or a combination thereof), and a photoinitiator.

In some embodiments, the functional materials may comprise polymethylmethacrylate (PMMA) resin solution, polystyrene (PS) resin solution, styrene resin solution, or a combination thereof. In some embodiments, the resin solutions comprise polymethylmethacrylate (PMMA) resin solution, polystyrene (PS) resin solution, styrene resin solution, inorganic or organic radiopacity materials, or a combination thereof. In some embodiments, the resin solutions may act as monomers and/or comonomers.

In some embodiments, the polymeric resin (110; e.g., the photosensitive polymeric resin) may comprise about 10 to 98% W/W or V/V of the resin solution. In some embodiments, the polymeric resin (110; e.g., the photosensitive polymeric resin) may comprise about 50 to 80% W/W or V/V of the resin solution. In some embodiments, the polymeric resin (110; e.g., the photosensitive polymeric resin) may comprise about 75 to 80% W/W or V/V of the resin solution.

In some embodiments, the polymeric resin (110; e.g., the photosensitive polymeric resin) may comprise about 10 to 98%, or about 10 to 95%, or about 10 to 90%, or about 10 to 85%, or about 10 to 80%, or about 10 to 75%, or about 10 to 70%, or about to 65%, or about 10 to 60%, or about 10 to 50%, or about 10 to 40%, or about 10 to 30%, or about 10 to 20% W/W or V/V of the resin solution. In some embodiments, the polymeric resin (110; e.g., the photosensitive polymeric resin) may comprise about 20 to 98%, or about 20 to 95%, or about 20 to 90%, or about 20 to 85%, or about 20 to 80%, or about 20 to 75%, or about 20 to 70%, or about 20 to 65%, or about 20 to 60%, or about to 50%, or about 20 to 40%, or about 20 to 30% W/W or V/V of the resin solution. In some embodiments, the polymeric resin (110; e.g., the photosensitive polymeric resin) may comprise about 30 to 98%, or about 30 to 95%, or about 30 to 90%, or about 30 to 85%, or about 30 to 80%, or about 30 to 75%, or about 30 to 70%, or about 30 to 65%, or about 30 to 60%, or about 30 to 50%, or about 30 to 40% W/W or V/V of the resin solution. In some embodiments, the polymeric resin (110; e.g., the photosensitive polymeric resin) may comprise about 40 to 98%, or about 40 to 95%, or about 40 to 90%, or about 40 to 85%, or about 40 to 80%, or about 40 to 75%, or about 40 to 70%, or about 40 to 65%, or about 40 to 60%, or about 40 to 50% W/W or V/V of the resin solution. In some embodiments, the polymeric resin (110; e.g., the photosensitive polymeric resin) may comprise about 50 to 98%, or about 50 to 95%, or about 50 to 90%, or about 50 to 85%, or about 50 to 80%, or about 50 to 75%, or about 50 to 70%, or about 50 to 65%, or about 50 to 60% W/W or V/V of the resin solution.

In some embodiments, the polymeric resin (110; e.g., the photosensitive polymeric resin) may comprise about 60 to 98%, or about 60 to 95%, or about 60 to 90%, or about 60 to 85%, or about 60 to 80%, or about 60 to 75%, or about 60 to 70%, or about to 65%, or about 65 to 98%, or about 65 to 95%, or about 65 to 90%, or about 65 to 85%, or about 65 to 80%, or about 65 to 75%, or about 65 to 70%, W/W or V/V of the resin solution. In some embodiments, the polymeric resin (110; e.g., the photosensitive polymeric resin) may comprise about 70 to 98%, or about 70 to 95%, or about 70 to 90%, or about 70 to 85%, or about 70 to 80%, or about 70 to 75%, or about 75 to 98%, or about to 95%, or about 75 to 90%, or about 75 to 85%, or about 75 to 80% W/W or V/V of the resin solution. In some embodiments, the polymeric resin (110; e.g., the photosensitive polymeric resin) may comprise about 80 to 98%, or about 80 to 95%, or about 80 to 90%, or about 80 to 85%, or about 80 to 98%, or about 80 to 95%, or about 80 to 90%, or about 80 to 85% W/W or V/V of the resin solution. In some embodiments, the polymeric resin (110; e.g., the photosensitive polymeric resin) may comprise about 90 to 98%, or about 90 to 95%, or about 95 to 98% W/W or V/V of the resin solution.

In some embodiments, the polymeric resin (110; e.g., the photosensitive polymeric resin) may comprise about 98% W/W or V/V of the resin solution. In some embodiments, the polymeric resin (110; e.g., the photosensitive polymeric resin) may comprise about 95% W/W or V/V of the resin solution. In some embodiments, the polymeric resin (110; e.g., the photosensitive polymeric resin) may comprise about 90% W/W or V/V of the resin solution. In some embodiments, the polymeric resin (110; e.g., the photosensitive polymeric resin) may comprise about 85% W/W or V/V of the resin solution. In some embodiments, the polymeric resin (110; e.g., the photosensitive polymeric resin) may comprise about 80% W/W or V/V of the resin solution. In some embodiments, the polymeric resin (110; e.g., the photosensitive polymeric resin) may comprise about 75% W/W or V/V of the resin solution. In some embodiments, the polymeric resin (110; e.g., the photosensitive polymeric resin) may comprise about 70% W/W or V/V of the resin solution. In some embodiments, the polymeric resin (110; e.g., the photosensitive polymeric resin) may comprise about 65% W/W or V/V of the resin solution. In some embodiments, the polymeric resin (110; e.g., the photosensitive polymeric resin) may comprise about 60% W/W or V/V of the resin solution. In some embodiments, the polymeric resin (110; e.g., the photosensitive polymeric resin) may comprise about 50% W/W or V/V of the resin solution. In some embodiments, the polymeric resin (110; e.g., the photosensitive polymeric resin) may comprise about 40% W/W or V/V of the resin solution. In some embodiments, the polymeric resin (110; e.g., the photosensitive polymeric resin) may comprise about 30% W/W or V/V of the resin solution. In some embodiments, the polymeric resin (110; e.g., the photosensitive polymeric resin) may comprise about 20% W/W or V/V of the resin solution. In some embodiments, the polymeric resin (110; e.g., the photosensitive polymeric resin) may comprise about 10% W/W or V/V of the resin solution.

In some embodiments, the polymeric resin (110; e.g., the photosensitive polymeric resin) may comprise about 1 to 50% W/W or V/V of a comonomer. In some embodiments, the polymeric resin (110; e.g., the photosensitive polymeric resin) may comprise about 5 to 20% W/W or V/V of a comonomer.

In some embodiments, the polymeric resin (110; e.g., the photosensitive polymeric resin) may comprise about 0.5 to 50%, or about 0.5 to 40%, or about 0.5 to 30%, or about 0.5 to 20%, or about 0.5 to 15%, or about 0.5 to 10%, or about 0.5 to 5%, or about 5 to 50%, or about 5 to 40%, or about 5 to 30%, or about 5 to 20%, or about 5 to 15%, or about 5 to 10% W/W or V/V of a comonomer. In some embodiments, the polymeric resin (110; e.g., the photosensitive polymeric resin) may comprise about 10 to 50%, or about 10 to 40%, or about 10 to 30%, or about 10 to 20%, or about 10 to 15%, to 50%, or about 15 to 40%, or about 15 to 30%, or about 15 to 20%, or about 20 to 50%, or about 20 to 40%, or about 20 to 30%, or about 30 to 50%, or about 30 to 40%, or about 40 to 50% W/W or V/V of a comonomer.

The polymeric resin (110; e.g., the photosensitive polymeric resin) may comprise one or more crosslinkers (e.g., a short chain crosslinker, a long chain crosslinker, or a combination thereof). In some embodiments, the polymeric resin (110; e.g., the photosensitive polymeric resin) may comprise 0.1 to 40% W/W or V/V of a crosslinker.

In some embodiments, the polymeric resin (110; e.g., the photosensitive polymeric resin) may comprise about 0.1 to 40%, or about 0.1 to 30%, or about 0.1 to 20%, or about 0.1 to 10%, or about 0.1 to 5%, or about 0.1 to 1%, or about 1 to 40%, or about 1 to 30%, or about 1 to 20%, or about 1 to 10%, or about 1 to 5%, or about 5 to 40%, or about 5 to 30%, or about 5 to 20%, or about 5 to 10%, or about 10 to 40%, or about 10 to 30%, or about 10 to 20%, or about 20 to 40%, or about 20 to 30%, or about 30 to 40% W/W or V/V of a crosslinker.

In some embodiments, the polymeric resin (110; e.g., the photosensitive polymeric resin) may comprise 0.1 to 40%

W/W or V/V of one or more short chain crosslinkers. In some embodiments, the polymeric resin (110; e.g., the photosensitive polymeric resin) may comprise 0.1 to 20% W/W or V/V of one or more short chain crosslinkers. In some embodiments, the polymeric resin (110; e.g., the photosensitive polymeric resin) may comprise about 0.1 to 40%, or about 0.1 to 30%, or about 0.1 to 20%, or about 0.1 to 10%, or about 0.1 to 5%, or about 0.1 to 1%, or about 1 to 40%, or about 1 to 30%, or about 1 to 20%, or about 1 to 10%, or about 1 to 5%, or about 5 to 40%, or about 5 to 30%, or about 5 to 20%, or about 5 to 10%, or about 10 to 40%, or about 10 to 30%, or about 10 to 20%, or about 20 to 40%, or about 20 to 30%, or about to 40% W/W or V/V of one or more short chain crosslinkers.

In some embodiments, the polymeric resin (110; e.g., the photosensitive polymeric resin) may comprise 0.1 to 40% W/W or V/V of one or more long-chain crosslinkers. In some embodiments, the polymeric resin (110; e.g., the photosensitive polymeric resin) may comprise 0.1 to 20% W/W or V/V of one or more long-chain crosslinkers. In some embodiments, the polymeric resin (110; e.g., the photosensitive polymeric resin) may comprise about 0.1 to 40%, or about 0.1 to 30%, or about 0.1 to 20%, or about 0.1 to 10%, or about 0.1 to 5%, or about 0.1 to 1%, or about 1 to 40%, or about 1 to 30%, or about 1 to 20%, or about 1 to 10%, or about 1 to 5%, or about 5 to 40%, or about 5 to 30%, or about 5 to 20%, or about 5 to 10%, or about 10 to 40%, or about 10 to 30%, or about 10 to 20%, or about 20 to 40%, or about 20 to 30%, or about 30 to 40% W/W or V/V of one or more long-chain crosslinkers.

In some embodiments, the functional materials may comprise cyclohexyl methacrylate, isobornyl methacrylate, butyl acrylate, Isodecyl methacrylate, Tetrahydrofurfuryl methacrylate, Lauryl methacrylate, Isodecyl methacrylate, Lauryl acrylate or a combination thereof. The aforementioned functional materials may act as monomers and comonomers to enable the polymerization of the polymeric resin.

In some embodiments, the polymeric resin (110; e.g., the photosensitive polymeric resin) may comprise about 0.5 to 50% W/W or V/V of a functional material that acts as a monomer and comonomer to enable the polymerization of the polymeric resin. In some embodiments, the polymeric resin (110; e.g., the photosensitive polymeric resin) may comprise about 5 to 15% W/W or V/V of a functional material that acts as a monomer and comonomer to enable the polymerization of the polymeric resin.

In some embodiments, the polymeric resin (110; e.g., the photosensitive polymeric resin) may comprise about 0.5 to 50%, or about 0.5 to 40%, or about 0.5 to 30%, or about 0.5 to 20%, or about 0.5 to 15%, or about 0.5 to 10%, or about 0.5 to 5%, or about 1 to 50%, or about 1 to 40%, or about 1 to 30%, or about 1 to 20%, or about 1 to 15%, or about 1 to 10%, or about 1 to 5%, or about 5 to 50%, or about 5 to 40%, or about to 30%, or about 5 to 20%, or about 5 to 15%, or about 5 to 10% W/W or V/V of a functional material that acts as a monomer and comonomer to enable the polymerization of the polymeric resin. In some embodiments, the polymeric resin (110; e.g., the photosensitive polymeric resin) may comprise about 10 to 50%, or about 10 to 40%, or about 10 to 30%, or about 10 to 20%, or about 10 to 15%, or about 15 to 50%, or about to 40%, or about 15 to 30%, or about 15 to 20%, or about 20 to 50%, or about 20 to 40%, or about 20 to 30%, or about 30 to 50%, or about 30 to 40%, or about 40 to 50% W/W or V/V of a functional material that acts as a monomer and comonomer to enable the polymerization of the polymeric resin.

In some embodiments, the polymeric resin (110; e.g., the photosensitive polymeric resin) may comprise about 0.5% W/W or V/V of a functional material that acts as a monomer and comonomer to enable the polymerization of the polymeric resin. In some embodiments, the polymeric resin (110; e.g., the photosensitive polymeric resin) may comprise about 5% W/W or V/V of a functional material that acts as a monomer and comonomer to enable the polymerization of the polymeric resin. In some embodiments, the polymeric resin (110; e.g., the photosensitive polymeric resin) may comprise about 10% W/W or V/V of a functional material that acts as a monomer and comonomer to enable the polymerization of the polymeric resin. In some embodiments, the polymeric resin (110; e.g., the photosensitive polymeric resin) may comprise about 15% W/W or V/V of a functional material that acts as a monomer and comonomer to enable the polymerization of the polymeric resin. In some embodiments, the polymeric resin (110; e.g., the photosensitive polymeric resin) may comprise about 20% W/W or V/V of a functional material that acts as a monomer and comonomer to enable the polymerization of the polymeric resin. In some embodiments, the polymeric resin (110; e.g., the photosensitive polymeric resin) may comprise about 30% W/W or V/V of a functional material that acts as a monomer and comonomer to enable the polymerization of the polymeric resin. In some embodiments, the polymeric resin (110; e.g., the photosensitive polymeric resin) may comprise about 40% W/W or V/V of a functional material that acts as a monomer and comonomer to enable the polymerization of the polymeric resin. In some embodiments, the polymeric resin (110; e.g., the photosensitive polymeric resin) may comprise about 50% W/W or V/V of a functional material that acts as a monomer and comonomer to enable the polymerization of the polymeric resin.

In some embodiments, the functional materials may comprise diurethane dimethacrylate, triethylene glycol dimethacrylate, 1,6-Hexanediol dimethacrylate, Trimethylolpropane triacrylate, Pentaerythritol tetraacrylate, Di(trimethylolpropane) tetraacrylate or a combination thereof. The aforementioned functional materials may act as monomers, comonomers, and crosslinkers to enable the polymerization of the polymeric resin.

In some embodiments, the polymeric resin (110; e.g., the photosensitive polymeric resin) may comprise about 0.5 to 50% W/W or V/V of a functional material that acts as a monomer, comonomer, and crosslinker to enable the polymerization of the polymeric resin. In some embodiments, the polymeric resin (110; e.g., the photosensitive polymeric resin) may comprise about 1 to 10% W/W or V/V of a functional material that acts as a monomer, comonomer, and crosslinker to enable the polymerization of the polymeric resin.

In some embodiments, the polymeric resin (110; e.g., the photosensitive polymeric resin) may comprise about 0.1 to 50%, or about 0.1 to 40%, or about 0.1 to 30%, or about 0.1 to 20%, or about 0.1 to 15%, or 0.1 to 10%, or about 0.1 to 5%, or 0.1 to 1%, about 0.5 to 50%, or about 0.5 to 40%, or about 0.5 to 30%, or about 0.5 to 20%, or about 0.5 to 15%, or about 0.5 to 10%, or about 0.5 to 5%, or about 0.5 to 1%, or about 1 to 50%, or about 1 to 40%, or about 1 to 30%, or about 1 to 20%, or about 1 to 15%, or about 1 to 10%, or about 1 to 5%, or about 5 to 50%, or about 5 to 40%, or about 5 to 30%, or about 5 to 20%, or about 5 to 15%, or about 5 to 10%, or about 10 to 50%, or about 10 to 40%, or about 10 to 30%, or about 10 to 20%, or about 10 to 15%, or about 15 to 50%, or about 15 to 40%, or about 15 to 30%, or about 15 to 20%, or about 20 to 50%, or about 20 to 40%, or about 20 to 30%, or about 30 to 50%, or about 30 to 40%, or about 40 to 50% W/W or V/V of a functional material that acts as a monomer, comonomer, and crosslinker to enable the polymerization of the polymeric resin.

In some embodiments, the polymeric resin (110; e.g., the photosensitive polymeric resin) may comprise about 0.1% W/W or V/V of a functional material that acts as a monomer, comonomer, and crosslinker to enable the polymerization of the polymeric resin. In some embodiments, the polymeric resin (110; e.g., the photosensitive polymeric resin) may comprise about 0.5% W/W or V/V of a functional material that acts as a monomer, comonomer, and crosslinker to enable the polymerization of the polymeric resin. In some embodiments, the polymeric resin (110; e.g., the photosensitive polymeric resin) may comprise about 1% W/W or V/V of a functional material that acts as a monomer, comonomer, and crosslinker to enable the polymerization of the polymeric resin. In some embodiments, the polymeric resin (110; e.g., the photosensitive polymeric resin) may comprise about 5% W/W or V/V of a functional material that acts as a monomer, comonomer, and crosslinker to enable the polymerization of the polymeric resin. In some embodiments, the polymeric resin (110; e.g., the photosensitive polymeric resin) may comprise about 10% W/W or V/V of a functional material that acts as a monomer, comonomer, and crosslinker to enable the polymerization of the polymeric resin. In some embodiments, the polymeric resin (110; e.g., the photosensitive polymeric resin) may comprise about 15% W/W or V/V of a functional material that acts as a monomer, comonomer, and crosslinker to enable the polymerization of the polymeric resin. In some embodiments, the polymeric resin (110; e.g., the photosensitive polymeric resin) may comprise about 20% W/W or V/V of a functional material that acts as a monomer, comonomer, and crosslinker to enable the polymerization of the polymeric resin. In some embodiments, the polymeric resin (110; e.g., the photosensitive polymeric resin) may comprise about 30% W/W or V/V of a functional material that acts as a monomer, comonomer, and crosslinker to enable the polymerization of the polymeric resin. In some embodiments, the polymeric resin (110; e.g., the photosensitive polymeric resin) may comprise about 40% W/W or V/V of a functional material that acts as a monomer, comonomer, and crosslinker to enable the polymerization of the polymeric resin. In some embodiments, the polymeric resin (110; e.g., the photosensitive polymeric resin) may comprise about 50% W/W or V/V of a functional material that acts as a monomer, comonomer, and crosslinker to enable the polymerization of the polymeric resin.

In some embodiments, the functional materials may comprise ethylene glycol dimethacrylate, Di(ethylene glycol) dimethacrylate, tetraethylene glycol dimethacrylate, triethylene glycol dimethacrylate, or a combination thereof. The aforementioned functional materials may act as short-chain, non-degradable crosslinkers to improve the stiffness of the cured polymer.

In some embodiments, the polymeric resin (110; e.g., the photosensitive polymeric resin) may comprise about 0.1 to 10% W/W or V/V of a functional material that acts as a short-chain, non-degradable crosslinker to improve the stiffness of the cured polymer. In some embodiments, the polymeric resin (110; e.g., the photosensitive polymeric resin) may comprise about 0.1 to 5% W/W or V/V of a functional material that acts as a short-chain, non-degradable crosslinker to improve with the stiffness of the cured polymer.

In some embodiments, the polymeric resin (110; e.g., the photosensitive polymeric resin) may comprise about 0.1 to 10%, or about 0.1 to 9%, or about 0.1 to 8%, or about 0.1 to 7%, or about 0.1 to 6%, or about 0.1 to 5%, or about 0.1 to 4%, or about to 3%, or about 0.1 to 2%, or about 0.1 to 1%, or about 0.1 to 0.5%, or about 0.5 to 10%, or about 0.5 to 9%, or about 0.5 to 8%, or about 0.5 to 7%, or about 0.5 to 6%, or about 0.5 to 5%, or about 0.5 to 4%, or about 0.5 to 3%, or about 0.5 to 2%, or about 0.5 to 1%, or about W/W or V/V a functional material that acts as a short-chain, non-degradable crosslinker to improve the stiffness of the cured polymer. In some embodiments, the polymeric resin (110; e.g., the photosensitive polymeric resin) may comprise about 1 to 10%, or about 1 to 9%, or about 1 to 8%, or about 1 to 7%, or about 1 to 6%, or about 1 to 5%, or about 1 to 4%, or about 1 to 3%, or about 1 to 2%, or about 2 to 10%, or about 2 to 9%, or about 2 to 8%, or about 2 to 7%, or about 2 to 6%, or about 2 to 5%, or about 2 to 4%, or about 2 to 3%, or about 3 to 10%, or about 3 to 9%, or about 3 to 8%, or about 3 to 7%, or about 3 to 6%, or about 3 to 5%, or about 3 to 4% W/W or V/V of a functional material that acts as a short-chain, non-degradable crosslinker to improve the stiffness of the cured polymer. In some embodiments, the polymeric resin (110; e.g., the photosensitive polymeric resin) may comprise about 4 to 10%, or about 4 to 9%, or about 4 to 8%, or about 4 to 7%, or about 4 to 6%, or about 4 to 5%, or about 5 to 10%, or about 5 to 9%, or about 5 to 8%, or about 5 to 7%, or about 5 to 6%, or about 6 to 10%, or about 6 to 9%, or about 6 to 8%, or about 6 to 7%, or about 7 to 10%, or about 7 to 9%, or about 7 to 8%, or about 8 to 10%, or about 8 to 9%, or about 9 to 10% W/W or V/V of a functional material that acts as a short-chain, non-degradable crosslinker to improve the stiffness of the cured polymer.

In some embodiments, the polymeric resin (110; e.g., the photosensitive polymeric resin) may comprise about 0.1% W/W or V/V of a functional material that acts as a short-chain, non-degradable crosslinker to improve the stiffness of the cured polymer. In some embodiments, the polymeric resin (110; e.g., the photosensitive polymeric resin) may comprise about 0.5% W/W or V/V of a functional material that acts as a short-chain, non-degradable crosslinker to improve the stiffness of the cured polymer. In some embodiments, the polymeric resin (110; e.g., the photosensitive polymeric resin) may comprise about 1% W/W or V/V of a functional material that acts as a short-chain, non-degradable crosslinker to improve the stiffness of the cured polymer. In some embodiments, the polymeric resin (110; e.g., the photosensitive polymeric resin) may comprise about 2% W/W or V/V of a functional material that acts as a short-chain, non-degradable crosslinker to improve the stiffness of the cured polymer. In some embodiments, the polymeric resin (110; e.g., the photosensitive polymeric resin) may comprise about 3% W/W or V/V of a functional material that acts as a short-chain, non-degradable crosslinker to improve the stiffness of the cured polymer. In some embodiments, the polymeric resin (110; e.g., the photosensitive polymeric resin) may comprise about 4% W/W or V/V of a functional material that acts as a short-chain, non-degradable crosslinker to improve the stiffness of the cured polymer. In some embodiments, the polymeric resin (110; e.g., the photosensitive polymeric resin) may comprise about 5% W/W or V/V of a functional material that acts as a short-chain, non-degradable crosslinker to improve the stiffness of the cured polymer. In some embodiments, the polymeric resin (110; e.g., the photosensitive polymeric resin) may comprise about 6% W/W or V/V of a functional material that acts as a short-chain, non-degradable crosslinker to improve the stiffness of the cured polymer. In some embodiments, the polymeric resin (110; e.g., the photosensitive polymeric resin) may comprise about 7% W/W or V/V of a functional material that acts as a short-chain, non-degradable crosslinker to improve the stiffness of the cured polymer. In some embodiments, the polymeric resin (110; e.g., the photosensitive polymeric resin) may comprise about 8% W/W or V/V of a functional material that acts as a short-chain, non-degradable crosslinker to improve the stiffness of the cured polymer. In some embodiments, the polymeric resin (110; e.g., the photosensitive polymeric resin) may comprise about 9% W/W or V/V of a functional material that acts as a short-chain, non-degradable crosslinker to improve the stiffness of the cured polymer. In some embodiments, the polymeric resin (110; e.g., the photosensitive polymeric resin) may comprise about 10% W/W or V/V of a functional material that acts as a short-chain, non-degradable crosslinker to improve the stiffness of the cured polymer.

In some embodiments, the functional materials may comprise polycaprolactone dimethacrylate, polycaprolactone diacrylate, polycaprolactone trimethacrylate, or a combination thereof. The aforementioned functional materials may act as long-chain biodegradable crosslinkers, monomers, and comonomers to enable the removal of the cured polymer.

In some embodiments, the polymeric resin (110; e.g., the photosensitive polymeric resin) may comprise about 0.1 to 20% W/W or V/V of a functional material that acts as a long chain biodegradable crosslinker, monomer, and comonomer to enable the removal of the cured polymer. In some embodiments, the polymeric resin (110; e.g., the photosensitive polymeric resin) may comprise about 0.1 to 5% W/W or V/V of a functional material that acts as a long-chain biodegradable crosslinker, monomer, and comonomer to enable the removal of the cured polymer.

In some embodiments, the polymeric resin (110; e.g., the photosensitive polymeric resin) may comprise about 0.1 to 20%, or about 0.1 to 15% or about 0.1 to 10%, or about 0.1 to 5%, or about 0.1 to 4%, or about 0.1 to 3%, or about 0.1 to 2% or about 0.1 to 1%, or about 0.1 to 0.5%, or about 0.5 to 20%, or about 0.5 to 15% or about 0.5 to 10%, or about 0.5 to 5%, or about 0.5 to 4%, or about 0.5 to 3%, or about 0.5 to 2% or about 0.5 to 1% W/W or V/V of a functional material that acts as a long-chain biodegradable crosslinker, monomer, and comonomer to enable the removal of the cured polymer.

In some embodiments, the polymeric resin (110; e.g., the photosensitive polymeric resin) may comprise about 1 to 20%, or about 1 to 15% or about 1 to 10%, or about 1 to 5%, or about 1 to 4%, or about 1 to 3%, or about 1 to 2% or about 2 to 20%, or about 2 to 15% or about 2 to 10%, or about 2 to 5%, or about 2 to 4%, or about 2 to 3%, or about 3 to 20%, or about 3 to 15% or about 3 to 10%, or about 3 to 5%, or about 3 to 4%, or about 4 to 20%, or about 4 to 15% or about 4 to 10%, or about 4 to 5%, or about to 20%, or about 5 to 15% or about 5 to 10%, or about 10 to 20%, or about 10 to 15% or about 15 to 20% W/W or V/V of a functional material that acts as a long-chain biodegradable crosslinker, monomer, and comonomer to enable the removal of the cured polymer.

In some embodiments, the polymeric resin (110; e.g., the photosensitive polymeric resin) may comprise about 0.1% W/W or V/V of a functional material that acts as a long-chain biodegradable crosslinker, monomer, and comonomer to enable the removal of the cured polymer. In some embodiments, the polymeric resin (110; e.g., the photosensitive polymeric resin) may comprise about 0.5% W/W or V/V of a functional material that acts as a long-chain biodegradable crosslinker, monomer, and comonomer to enable the removal of the cured polymer. In some embodiments, the polymeric resin (110; e.g., the photosensitive polymeric resin) may comprise about 1% W/W or V/V of a functional material that acts as a long-chain biodegradable crosslinker, monomer, and comonomer to enable the removal of the cured polymer. In some embodiments, the polymeric resin (110; e.g., the photosensitive polymeric resin) may comprise about 2% W/W or V/V of a functional material that acts as a long-chain biodegradable crosslinker, monomer, and comonomer to enable the removal of the cured polymer. In some embodiments, the polymeric resin (110; e.g., the photosensitive polymeric resin) may comprise about 3% W/W or V/V of a functional material that acts as a long-chain biodegradable crosslinker, monomer, and comonomer to enable the removal of the cured polymer. In some embodiments, the polymeric resin (110; e.g., the photosensitive polymeric resin) may comprise about 4% W/W or V/V of a functional material that acts as a long-chain biodegradable crosslinker, monomer, and comonomer to enable the removal of the cured polymer. In some embodiments, the polymeric resin (110; e.g., the photosensitive polymeric resin) may comprise about 5% W/W or V/V of a functional material that acts as a long-chain biodegradable crosslinker, monomer, and comonomer to enable the removal of the cured polymer. In some embodiments, the polymeric resin (110; e.g., the photosensitive polymeric resin) may comprise about 10% W/W or V/V of a functional material that acts as a long-chain biodegradable crosslinker, monomer, and comonomer to enable the removal of the cured polymer. In some embodiments, the polymeric resin (110; e.g., the photosensitive polymeric resin) may comprise about 15% W/W or V/V of a functional material that acts as a long-chain biodegradable crosslinker, monomer, and comonomer to enable the removal of the cured polymer. In some embodiments, the polymeric resin (110; e.g., the photosensitive polymeric resin) may comprise about 20% W/W or V/V of a functional material that acts as a long-chain biodegradable crosslinker, monomer, and comonomer to enable the removal of the cured polymer.

In some embodiments, the functional materials comprise a polymethylmethacrylate (PMMA) resin solution, isobornyl methacrylate, diurethane dimethacrylate, ethylene glycol dimethacrylate, polycaprolactone dimethacrylate, or a combination thereof. The functional materials may further comprise 1-Phenyl-2-propen-1-one, trimethylolpropane triacrylate, Pentaerythritol tetraacrylate, glycerol propoxylate (1PO/OH), tris[2-(acryloyloxy)ethyl] isocyanurate, triacrylatepentaerythritol tetraacrylate, di pentaerythritol penta-/hexa-acrylate, trimethylolpropane tri methacrylate, triethylene glycol dimethacrylate, butyl acrylate, methacrylic acid, n-decyl methacrylate, 3,3,5-Trimethylcyclohexyl methacrylate, n-propyl methacrylate, n-propyl acrylate, benzyl methacrylate, N-butyl-methacrylate, n-octyl methacrylate, phenyl methacrylate, iso-Decyl acrylate, n-hexyl acrylate, sec-butyl methacrylate, iso-butyl methacrylate, cyclohexyl methacrylate, 2-phenoxyethyl methacrylate, sec-butyl acrylate, 2-methoxyethyl acrylate, ethyl methacrylate, 2-hydroxyethyl methacrylate, 2-ethylhexyl methacrylate, ethylene glycol-based dimethacrylates, 2-n-butoxyethyl methacrylate, 2-[4'-iodobenzoyloxy]ethyl methacrylate, 2-[2',3',5'-triiodobenzoyloxy]ethyl methacrylate, or a combination thereof.

In some embodiments, the selection and formulation of the functional materials enable cured polymers to be pulverizable. In some embodiments, the diurethane dimethacrylate, the ethylene glycol dimethacrylate, and polycaprolactone dimethacrylate allow the cured polymer to be pulverizable. In some embodiments, the selection and formulation of the functional materials allow the cured polymer to shrink in volume by less than 2% compared to the original volume of the uncured polymer. In some embodiments, the polymethylmethacrylate (PMMA) resin solution, isobornyl methacrylate, diurethane dimethacrylate, the ethylene glycol dimethacrylate, and the polycaprolactone dimethacrylate allows the cured polymer to shrink in volume by less than 2% as compared to the original volume of the uncured polymer.

In some embodiments, the functional materials comprise about 10-98% W/W or V/V of the PMMA resin solution, about 0.5-50% W/W or V/V of isobornyl methacrylate, about 0.5-50% W/W or V/V of diurethane dimethacrylate, about 0.1-10% W/W or V/V of ethylene glycol dimethacrylate, about 0.1-10% W/W or V/V of polycaprolactone dimethacrylate, and about 0.1-10% W/W or V/V of Diphenyl(2, 4, 6-trimethylbenzoyl) phosphine oxide.

In some embodiments, the functional materials comprise about 10-98% W/W or V/V of the PS resin solution, about 0.5-50% W/W or V/V of cyclohexyl methacrylate, about W/W or V/V of triethylene glycol dimethacrylate, about 0.1-10% W/W or V/V of di(ethylene glycol) dimethacrylate, about 0.1-10% W/W or V/V of polycaprolactone diacrylate, and about 0.1-10% W/W or V/V of Phenylbis(2,4,6-trimethylbenzoyl) phosphine oxide.

In other embodiments, the functional materials comprise about 10-98% W/W or V/V of the PMMA resin solution, about 0.5-50% W/W or V/V of butyl acrylate, about 0.5-50% W/W or V/V of 1,6-Hexanediol dimethacrylate, about 0.1-10% W/W or V/V of tetraethylene glycol, about 0.1-10% W/W or V/V of polycaprolactone trimethacrylate, and about 0.1-10% W/W or V/V of 2-Hydroxy-4'-(2-hydroxyethoxy)-2-methylpropiophenone.

In some embodiments, the functional materials comprise about 10-98% W/W or V/V of the polystyrene (PS) resin solution, about 0.5-50% W/W or V/V of isodecyl methacrylate, about 0.5-50% W/W or V/V of trimethylolpropane triacrylate, about 0.1-10% W/W or V/V of triethylene glycol dimethacrylate, about 0.1-10% W/W or V/V of polycaprolactone dimethacrylate, and about 0.1-10% W/W or V/V of 2,2'-Azobis(2-methylpropionitrile).

In some embodiments, the functional materials comprise about 10-98% W/W or V/V of the PMMA resin solution, about 0.5-50% W/W or V/V of lauryl methacrylate, about W/W or V/V of pentaerythritol tetraacrylate, about 0.1-10% W/W or V/V of ethylene glycol dimethacrylate, about 0.1-10% W/W or V/V of polycaprolactone diacrylate, and about 0.1-10% W/W or V/V of camphorquinone.

In some embodiments, the functional materials comprise about 75-80% W/W or V/V of the PMMA resin solution, about 5-15% W/W or V/V of isobornyl methacrylate, about 1-10% W/W or V/V of diurethane dimethacrylate, about 0.1-5% W/W or V/V of ethylene glycol dimethacrylate, about 0.1-5% W/W or V/V of polycaprolactone dimethacrylate, and about 0.1-2% W/W or V/V of Diphenyl(2, 4, 6-trimethylbenzoyl) phosphine oxide.

In other embodiments, the functional materials comprise about 75-80% W/W or V/V of the PMMA resin solution, about 5-15% W/W or V/V of cyclohexyl methacrylate, about 1-10% W/W or V/V of glycol dimethacrylate, about 0.1-5% W/W or V/V of ethylene glycol dimethacrylate, about 0.1-5% W/W or V/V of polycaprolactone diacrylate, and about W/W or V/V of Diphenyl(2, 4, 6-trimethylbenzoyl) phosphine oxide.

In some embodiments, the functional materials comprise about 75-80% W/W or V/V of the PMMA resin solution, about 5-15% W/W or V/V of isobornyl methacrylate, about 1-10% W/W or V/V of diurethane dimethacrylate, about 0.1-5% W/W or V/V of ethylene glycol dimethacrylate, about 0.1-5% W/W or V/V of polycaprolactone dimethacrylate, and about 0.1-2% W/W or V/V of Diphenyl(2, 4, 6-trimethylbenzoyl) phosphine oxide.

In some embodiments, the functional materials comprise about 75-80% W/W or V/V of the polystyrene (PS) resin solution, about 5-15% W/W or V/V of butyl acrylate, about 1-10% W/W or V/V of diurethane dimethacrylate, about 0.1-5% W/W or V/V of Di(ethylene glycol) dimethacrylate, about 0.1-5% W/W or V/V of polycaprolactone trimethacrylate, and about 0.1-2% WAN or V/V of 2,2'-Azobis(2-methylpropionitrile).

In some embodiments, the functional materials comprise about 75-80% W/W or V/V of the polystyrene (PS) resin solution, about 5-15% W/W or V/V of butyl acrylate, about 1-10% W/W or V/V of 1,6-hexanediol dimethacrylate, about 0.1-5% W/W or V/V of Di(ethylene glycol) dimethacrylate, about 0.1-5% W/W or V/V of polycaprolactone trimethacrylate, and about 0.1-2% W/W or V/V of Benzyl-2-(dimethylamino)-4'-morpholinobutyrophenone.

In certain embodiments, the functional materials comprise about 78.5% W/W or V/V of the PMMA resin solution, about 10% W/W or V/V of isobornyl methacrylate, about 5% W/W or V/V of diurethane dimethacrylate, about 3% W/W or V/V of ethylene glycol dimethacrylate, about 3% W/W or V/V of polycaprolactone dimethacrylate, and about W/W or V/V of Diphenyl(2, 4, 6-trimethylbenzoyl) phosphine oxide.

In some embodiments, functional material within the photocurable polymeric resin helps improve the cured polymer's performance. In some embodiments, the functional materials help limit volumetric shrinkage and improve the cured polymer's mechanical properties. Another critical factor for photocurable injection systems (100) is the synthesis and design of the functional materials that enable the cured polymer to be pulverizable, which helps in the extraction of the cured polymer. In some embodiments, the viscosity of the photocurable polymeric resin (110) is about 300 cP to 1500 cP. The viscosity of the photocurable polymeric resin (110) may depend on the concentration of the functional material and the desired depolymerization rate.

In some embodiments, the photocurable polymeric resin (110) liquid has a viscosity ranging from about 300 cP to about 400 cP. Low viscosity allows the filling of the expandable portion through a minimally invasive delivery system. In some embodiments, the viscosity of the free radical polymeric resin is about 500 cP to 10,000 cP. The viscosity of the non-photosensitive polymeric resin depends on the concentration of functional materials therein, polymer mixing speed, other variables (e.g., nitrogen atmosphere, vacuum), and depolymerization rate.

In some embodiments, the viscosity of the photocurable polymeric resin is about 300 cP to 1500 cP, or about 300 cP to 1000 cP, or about 300 cP to 800 cP, or about 300 cP to 600 cP, or about 300 cP to 500 cP, or about 300 cP to 400 cP, or about 400 cP to 1500 cP, or about 400 cP to 1000 cP, or about 400 cP to 800 cP, or about 400 cP to 600 cP, or about 400 cP to 500 cP, or about 500 cP to 1500 cP, or about 500 cP to 1000 cP, or about 500 cP to 800 cP, or about 500 cP to 600 cP, or about 600 cP to 1500 cP, or about 600 cP to 1000 cP, or about 600 cP to 800 cP, or about 800 cP to 1500 cP, or about 800 cP to 1000 cP, or about 1000 cP to 1500 cP.

In some embodiments, the viscosity of the free-radical polymeric resin is about 500 cP to 10,000 cP, or about 500 cP to 8,000 cP, or about 500 cP to 6,000 cP, or about 500 cP to 4,000 cP, or about 500 cP to 2,000 cP, or about 500 cP to 1,000 cP, or about 1,000 cP to 10,000 cP, or about 1,000 cP to 8,000 cP, or about 1,000 cP to 6,000 cP, or about 1,000 cP to 4,000 cP, or about 1,000 cP to 2,000 cP, or about 2,000 cP to 10,000 cP, or about 2,000 cP to 8,000 cP, or about 2,000 cP to 6,000 cP, or about 2,000 cP to 4,000 cP, or about 4,000 cP to 10,000 cP, or about 4,000 cP to 8,000 cP, or about 4,000 cP to 6,000 cP, or about 6,000 cP to 10,000 cP, or about 6,000 cP to 8.00 cP, or about 8,000 cP to 10,000 cP.

In some embodiments, the polymeric resin may further comprise additives or fillers comprising polyesters, polycarbonates, acrylates, polyurethanes, cellulose nanocrystals, gold nanoparticles, surface thiol-modified nanoparticles, cellulose-modified surfaces, preceramic materials, or a combination thereof.

In some embodiments, the photocurable polymeric resin (110) further comprises smart materials (e.g., smart nanomaterials). The cured polymer may undergo further depolymerization with activation of the smart nanomaterials within the polymer. In some embodiments, the smart nanomaterials are surface modified with functional chemistry to move one or more of the absorption and excitation bands of the smart nanomaterials to near-infrared (IR) regions, such that the smart nanomaterials are activated with IR rays. In some embodiments, the smart nanomaterials comprise surface-modified nanoparticles, nanopowders, nanoclusters, upper conversion nanoparticles, or a combination thereof. In some embodiments, the surface of the smart nanomaterials is modified with sulfur-containing ligands, phosphine, amine, polymers, silica, thiol, polyethylene glycol, amine, carboxylic acids functional chemistry, or a combination thereof.

In some embodiments, the photocurable polymeric resin (110) further comprises trojan nanomaterials (e.g., modified gold nanomaterials). In some embodiments, the trojan material is blended with powder or liquid components in bone cement; trojan material may be incorporated in a liquid component photocured system. Combining trojan material with primary matrix material may be physical, chemical, or enzymatic; this new composite blend melts at or below 120° C.; provides sufficient time for the surgeon to remove the cement after thawing and before resolidifying, unlike the minimal time offered by existing bone types of cement in the market; this novel concept of crosslinking an existing high strength polymer to create a blended composite can be used not only for orthopedic but also consider dental, other surgical and non-surgical applications where removal of the implant is involved; this blended composite cement can be used within a sleeve, bag, fabric, balloon, or even be used in direct contact with bone without a sleeve, bag, balloon, fabrics.

In some embodiments, the trojan nanomaterials may be surface-modified with organic functional chemistry to move the absorption wavelength of said trojan nanomaterials to infrared (IR) regions, where said trojan nanomaterial may be activated with IR rays remotely, without touching the bone. In-situ depolymerization may thus occur to remove the cured material with sleeves in a noninvasive fashion. The trojan materials may be activated using other mechanisms. For example, enzymes and thermal energy may optionally be utilized to assist in removing the implants of the present invention.

The current disclosure also focuses on more advanced technology to depolymerize polymeric resin/bone cement. Nanomaterials may be incorporated within resin materials and cured in this sophisticated system. Later, those nanomaterials may be activated with infrared rays to depolymerize. Since IR rays are not harmful to the body, irradiating using sources outside the body makes this process a non-invasive process.

In some embodiments, the present invention features a cross-linkable polymeric resin comprising ethylene glycol methacrylate, urethane diacrylate, bisacrylamide, aryl azide, carbodiimide, hydrazide, hydroxymethyl phosphine, imido ester, isocyanate, carbonyl, maleimide, NHS-ester, PFP-ester, psoralen, pyridyl disulfide, vinyl sulfone, derivatives of ethylene glycol di(meth)acrylate, derivatives of methylenebisacrylamide, formaldehyde-free crosslinking agent, divinylbenzene, or a combination thereof.

In some embodiments, the polymeric resin further comprises sensitivity enzymes, in vitro polymerization of artificial substrate monomers catalyzed by an isolated enzyme via non biosynthetic pathways. The enzymes can be used to synthesize oligomers and polymers of arylamines, e.g., aniline, substituted anilines, amino naphthalene, and its derivatives, catalyzed by oxidoreductases, such as laccases and peroxidases, in aqueous, organic, and mixed aqueous organic monophasic or biphasic media.

Ultrasonic System

The present invention features photocurable injection systems (100) that use a minimally invasive ultrasonic system for extracting the cured polymer. In some embodiments, the ultrasonic system comprises one or more ultrasonic probes. In some embodiments, the minimally invasive ultrasonic system may comprise one or more micro-sized ultrasonic probes.

Referring to FIGS. 2A-2E different ultrasonic probe structures and geometries enable access to the cured cement inside the canal through an access port. In some embodiments, the design includes the end shape and size of the probe, the size of the probe, and the structure to enable the outflow/extraction of the cured polymer. In some embodiments, the ultrasonic probes comprise titanium alloy materials that can match an acoustic sound to an ultrasonic sound. In some embodiments, the one or more ultrasonic probes (130) comprise a titanium or titanium-based alloy. In some embodiments, the shape of the one or more ultrasonic probes (130) comprises a hollow 3-dimensional shape with bends of 30°, 60°, or 90° (see FIG. 2B-2E).

Additionally, in some embodiments, the ultrasonic system may incorporate a vacuum. Without wishing to limit the present invention to any theory or mechanism, it is believed that combining a vacuum with the ultrasonic probes helps extract/remove the cured polymer (e.g., particles of the cured polymer) instead of using an external vacuum system. The customized ultrasonic probes are compatible with a minimally invasive approach through access ports, e.g., access ports on a sleeve device. Unlike commercially existing probes, the ultrasonic system is configured to utilize probes less than 3 mm that are designed specially to work through the access ports on a sleeve device and remove the cured bone cement.

In some embodiments, the ultrasonic probes may be less than about 5 mm in diameter and are designed specially to work through access ports and remove the cured polymer. In some embodiments, the ultrasonic probes are less than about 8 mm in diameter. In some embodiments, the ultrasonic probes are less than about 5 mm in diameter. In some embodiments, the ultrasonic probes are less than about 3 mm in diameter. In some embodiments, the ultrasonic probes are less than about 2 mm in diameter. In some embodiments, the ultrasonic probes are less than about 1 mm in diameter.

In some embodiments, the one or more ultrasonic probes are configured to enter a three-dimensional sleeve/bag/balloon (120) through one or more openings (122). The one or more ultrasonic probes may be configured to enable the outflow of a cured polymer through the one or more openings.

Sleeve Device

The systems and methods described herein may further comprise a sleeve device. As used herein, a "sleeve device" may be used interchangeably with the terms a sleeve, a bag, a balloon, a tube, or fabric, and may refer to a component that is inserted into a cavity (e.g., a medullary cavity or an intramedullary cavity) of a fractured bone before the polymeric resin (110) is inserted/injected into said cavity. In some embodiments, the polymeric resin (110) is injected into the sleeve device. In some embodiments, the sleeve device described herein enables controlled injection of the polymeric resin (110) without any air pockets.

In some embodiments, the sleeve device comprises an implantable three-dimensional biocompatible sleeve (120) comprising one or more openings (122), one or more access ports (124) disposed at the one or more openings (122), and a diffusive light guide tip (126) disposed through the one or more access ports (124). In some embodiments, the sleeve device may comprise a multilayer sleeve device. In some embodiments, the proximal and distal ends of the sleeves (120) have projected openings, one at each end. The sleeve (120) may further comprise a valve system that enables pressurized filling of photocurable polymeric resin (110) into the sleeve (120) located on the access above the port and in proximity to the external bone.

The sleeve device (120) may further comprise one or more access valves (e.g., duckbill or one-way valve or non-return valve mechanism) at a proximal end and/or distal end, connected to devices to detect and/or control the resin flow.

Non-limiting examples of material that may be used to construct the sleeve device include but are not limited to carbon lining, Dyneema fibers, Teflon-based sleeves, cellulose membranes, ultra-high molecular weight polyethylene linings, poly(vinylidene fluoride), poly(ethylene vinyl acetate), thermoplastic polyurethane, polyester fibers, or a combination thereof.

As used herein, an "optical guide," an "optical fiber," a "diffusive light guide tip," and/or a "light guide with a diffusive tip" may all be used interchangeably and may refer to a component of the sleeve device that is able to transmit light energy.

In some embodiments, the diffusive light guide tip (126; e.g., the optical fiber) is made from a biocompatible material. The diffusive light guide tip (126; e.g., the optical fiber) can transmit light energy from a UV-visible emitting light source. In some embodiments, the diffusive light guide tip (126) comprises a UV source with a spectrum of about 260 nm to 500 nm wavelength range and a visible light source with a spectrum of about 400 to 700 nanometers. In some embodiments, the wavelength of the UV source is about 260 nm to 500 nm, or about 260 nm to 450, or about 260 nm to 400 nm, or about 260 nm to 350 nm, or about 260 nm to 300 nm, or about 300 nm to 500 nm, or about 300 nm to 450 nm, or about 300 nm to 400 nm, or about 300 nm to 350 nm, or about 350 nm to 500 nm, or about 350 nm to 450 nm, or about 350 nm to 400 nm, or about 400 nm to 500 nm, or about 400 nm to 450 nm, or about 450 nm to 500 nm. In some embodiments, the wavelength of the visible light source is about 400 nm to 800 nm, or about 400 nm to 750 nm, or about 400 nm to 700 nm, or about 400 nm to 650 nm, or about 400 nm to 600 nm, or about 400 nm to 550 nm, or about 400 nm to 500 nm, or about 400 nm to 450 nm, or about 450 nm to 800 nm, about 450 nm to 700 nm, or about 450 nm to 650 nm, or about 450 nm to 600 nm, or about 450 nm to 550 nm, or about 450 nm to 500 nm, or about 500 nm to 800 nm, or about 500 nm to 700 nm, or about 500 nm to 650 nm, or about 500 nm to 600 nm, or about 500 nm to 550 nm, or about 550 nm to 700 nm, or about 550 nm to 650 nm, or about 550 nm to 600 nm, or 600 nm to 800 nm, or about 600 nm to 700 nm, or about 600 nm to 650 nm, or about 650 nm to 800 nm, or about 650 nm to 700 nm. In some embodiments, the diffusive light guide tip (126) comprises visible light with a wavelength spectrum of about 380 nm to about 780 nm, about 380 nm to about 600 nm, about 420 nm to about 500 nm, or about 450 nm to about 470 nm, which is used to cure the photocurable polymeric resin.

In some embodiments, the thickness of the diffusive light guide tip (126) is 0.5 mm to 2 mm. In some embodiments, the thickness of the diffusive light guide tip (126) is about 0.5 mm to 2.0 mm, or about 0.5 mm to 1.5 mm, or about 0.5 mm to 1.0 mm, or about 1.0 mm to 2.0 mm, or about 1.0 mm to 1.5 mm, or about 1.5 mm to 2.0 mm. In some embodiments, the UV-Visible light guide optical fiber can have a diameter of about mm, about 1 mm, about 1.5 mm, about 2 mm, less than about 0.75 mm, or greater than about 2 mm, as not all embodiments of the present disclosure are intended to be limited in this respect. In some embodiments, the thickness of the diffusive light guide tip (126) is selected based on the parameters of the patient.

In some embodiments, the diffusive light guide tip (126; e.g., the optical fiber) has a diameter of about 1.0 mm to 2.0 mm. In some embodiments, the optical fiber can have a diameter of about 0.5 mm, about 1.0 mm, about 1.5 mm, about 2.0 mm, less than about mm, or greater than about 2 mm, as not all embodiments of the present disclosure are intended to be limited in this respect.

The diffusive light guide tip (126; e.g., the optical fiber) can be made from any material, such as glass, silicon, silica glass, quartz, sapphire, plastic, combinations of materials, or any other material, and may have any diameter, as not all embodiments of the present disclosure are intended to be limited in this respect. In some embodiments, the optical fiber is made from a polymethyl methacrylate core with a transparent polymer cladding. In some embodiments, the diffuse tip comprises a biocompatible material, such as glass, silicon, silica glass, quartz, sapphire, plastic, or a combination thereof. In some embodiments, the optical light guide (126) comprises a coating of a biocompatible material, a biodegradable material, or a combination thereof.

In some embodiments, the diffusive light guide tip (126; e.g., the optical fiber) is made from a polymethyl methacrylate core with a transparent polymer cladding. It should be appreciated that the above-described characteristics and properties of the optical fibers are exemplary, and not all embodiments of the present disclosure are intended to be limited in these respects.

In some embodiments, the sleeve device may further comprise a sensor, a camera, or a combination thereof. In some embodiments, the sleeve device comprises one or more sensors and/or one or more cameras. In embodiments that utilize a multilayer sleeve device, the cameras (e.g., the one or more cameras) may be mounted between the layers of the sleeve. In some embodiments, the sensor may comprise a motion sensor, a pressure sensor, or a combination thereof.

In some embodiments, the camera (e.g., the one or more cameras) is about 0.2 mm to 0.5 mm in size. In some embodiments, the camera (e.g., the one or more cameras) is about 0.1 mm to 1.0 mm, or about 0.1 mm to 0.8 mm, or about 0.1 mm to 0.6 mm, or about 0.1 mm to 0.4 mm, or about 0.1 mm to 0.2 mm, or about 0.2 mm to 1.0 mm, or about 0.2 mm to 0.8 mm, or about 0.2 mm to 0.6 mm, or about 0.2 mm to 0.4 mm, or about 0.4 mm to 1.0 mm, or about 0.4 mm to 0.8 mm, or about 0.4 mm to 0.6 mm, or about 0.6 mm to 1.0 mm, or about 0.6 mm to 0.8 mm, or about 0.8 mm to 1.0 mm in size. In some embodiments, the camera (e.g., the one or more cameras) is less than 0.1 mm in size. In some embodiments, the camera (e.g., the one or more cameras) is greater than 1.0 mm in size.

In some embodiments, the sensor (e.g., the one or more sensors) has a diameter of about 0.2 mm to 0.5 mm. In some embodiments, the sensor (e.g., the one or more sensors) has a diameter of about 0.1 mm to 1.0 mm, or about 0.1 mm to 0.8 mm, or about mm to 0.6 mm, or about 0.1 mm to 0.4 mm, or about 0.1 mm to 0.2 mm, or about 0.2 mm to 1.0 mm, or about 0.2 mm to 0.8 mm, or about 0.2 mm to 0.6 mm, or about 0.2 mm to 0.4 mm, or about 0.4 mm to 1.0 mm, or about 0.4 mm to 0.8 mm, or about 0.4 mm to mm, or about 0.6 mm to 1.0 mm, or about 0.6 mm to 0.8 mm, or about 0.8 mm to 1.0 mm.

The sensors and/or camera described herein may further comprise a coating and/or outer material comprising the aforementioned functional materials (e.g., the same functional materials used in the photocurable polymeric resin) or other biocompatible materials.

In some embodiments, the curing and removal process may be monitored by modern sensors and cameras. Without wishing to limit the present invention to any theory or mechanism, it is believed that the sensors incorporated into the sleeve device can assist in placing the photocurable polymeric resin with pressure and removing the cured polymer. The sensor (e.g., a pressure and/or motion sensor) may be involved in guiding the photocurable injection system (100). The camera within the sleeve device may help visualize the injection process for the photocurable injection system (100) and/or the removal process of the cured polymer.

In some embodiments, the sleeve (120) further comprises a modified nanomaterial configured to be activated remotely without touching the implanted bone. Activation of the nanomaterial may result in depolymerization of the resin (110). The nanomaterial may be activated by IR rays, enzymes, thermal sources, or a combination thereof.

In some embodiments, the one or more ultrasonic probes are configured to contact a three-dimensional sleeve (120) by one or more openings (122). The one or more ultrasonic probes (130) may be configured to enable polymer outflow.

In some embodiments, the formulation of the photocurable polymeric resin comprising functional materials, the section of the sleeve device, and the curing process may be determined through a machine learning algorithm with artificial intelligence (AI) configured to consider patient ages, bone density, region of fracture, and classification of fracture. AI can help detect the formulation of polymeric resin (110) and the curing process with the preprogrammed machine learning system.

The systems described in this disclosure provide a non-absorbable solution for repairing and strengthening bones that can be left in place permanently or removed if desired.

Additional description of the aforestated sleeve device can be found in U.S. Provisional Patent Application No. 63/374,319, "METHODS FOR CREATING, INSERTING, AND REMOVING AN INTRAMEDULLARY SLEEVE SYSTEM FOR BONE TREATMENT AND STABILIZATION," filed Sep. 1, 2022, and the co-owned non-provisional application, the contents of which are hereby incorporated by reference in their entirety.

Methods

The present invention may also feature a method for repairing a bone fracture (e.g., in a subject in need thereof). The method may comprise a) injecting a photocurable polymeric resin (110) into a medullary cavity of a fractured bone, the photocurable polymeric resin (110) comprises functional materials that are adapted to photocure into the polymer, and the cured polymer is pulverizable, b) photopolymerizing the photocurable polymeric resin (110) in-situ using a diffusive light guide tip to produce a cured polymer (e.g., a high stiffness cured polymer), where the reaction temperature is at most 55 to 65° C., and a reaction temperature outside a sleeve device is at most 40° C.; additionally, the cured polymer shrinks in volume by less than 2% as compared to the original volume of the uncured polymer, c) pulverizing the cured polymer into particles using a minimally invasive ultrasonic system, and d) extracting the particles.

In some embodiment, the method comprises a) injecting a photocurable polymeric resin (110) into a medullary cavity of a fractured bone, the photocurable polymeric resin (110) comprises functional materials that are adapted to photocure into the polymer, and the cured polymer is pulverizable, b) photopolymerizing the photocurable polymeric resin (110) in-situ using a diffusive light guide tip to produce a cured polymer (e.g., a high stiffness cured polymer), where the reaction temperature is a physiological temperature (e.g., at most 40° C.); additionally, the cured polymer shrinks in volume by less than 2% as compared to the original volume of the uncured polymer, c) pulverizing the cured polymer into particles using a minimally invasive ultrasonic system, and d) extracting the particles.

The aforementioned method may further comprise injecting the photocurable polymeric resin (110) into a sleeve in the medullary cavity of the fractured bone. In some embodiments, the photocurable polymeric resin (110) is photocured into the polymer (e.g., a high stiffness cured polymer and/or a stiff cured polymer) inside the sleeve. When curing the photocurable polymeric resin (110) into the polymer inside the sleeve, the temperature outside the sleeve is at most 40° C.

The embodiments disclosed herein relate to minimally invasive orthopedic management procedures, particularly to photocurable injection systems for repair on the same day. In an embodiment, a photocurable injection system may include a multilayer and/or single-layer sleeve device comprising an expandable portion releasably mounted on a small diameter, flexible insertion sleeve. In some embodiments, the expandable portion is adapted to reside within an inner cavity of at least two bone fragments and provide support to the bone fragments. In some embodiments, the expandable portion is adapted to reside within an internal cavity of at least two bone fragments and secure the bone fragments in a relatively fixed relationship to each other, thus ensuring that the fractured bone can regenerate orientation and properly fuse the fracture.

In some embodiments, the photocurable injection systems (100) of the present disclosure are used to treat a fracture including, but not limited to, a hand fracture, a wrist fracture, a radius fracture, an ulna fracture, a clavicle fracture, a metacarpal fracture, a phalanx fracture, a metatarsal fracture, a phalange fracture, a tibia fracture, a fibula fracture, a humerus fracture, and a rib fracture. Long bones are the large bones in the arms and legs, including the humerus, radius/ulna, femur, and tibia/fibula. In an embodiment, a system of the present disclosure is used to reinforce a long bone fracture. In some embodiments, a system of the present disclosure is used to stabilize a long bone fracture in conjunction with anatomic reduction (i.e., proper reorientation of fractured elements to their original position, both relative to one another and relative to other adjacent anatomical features).

Figure 1B:
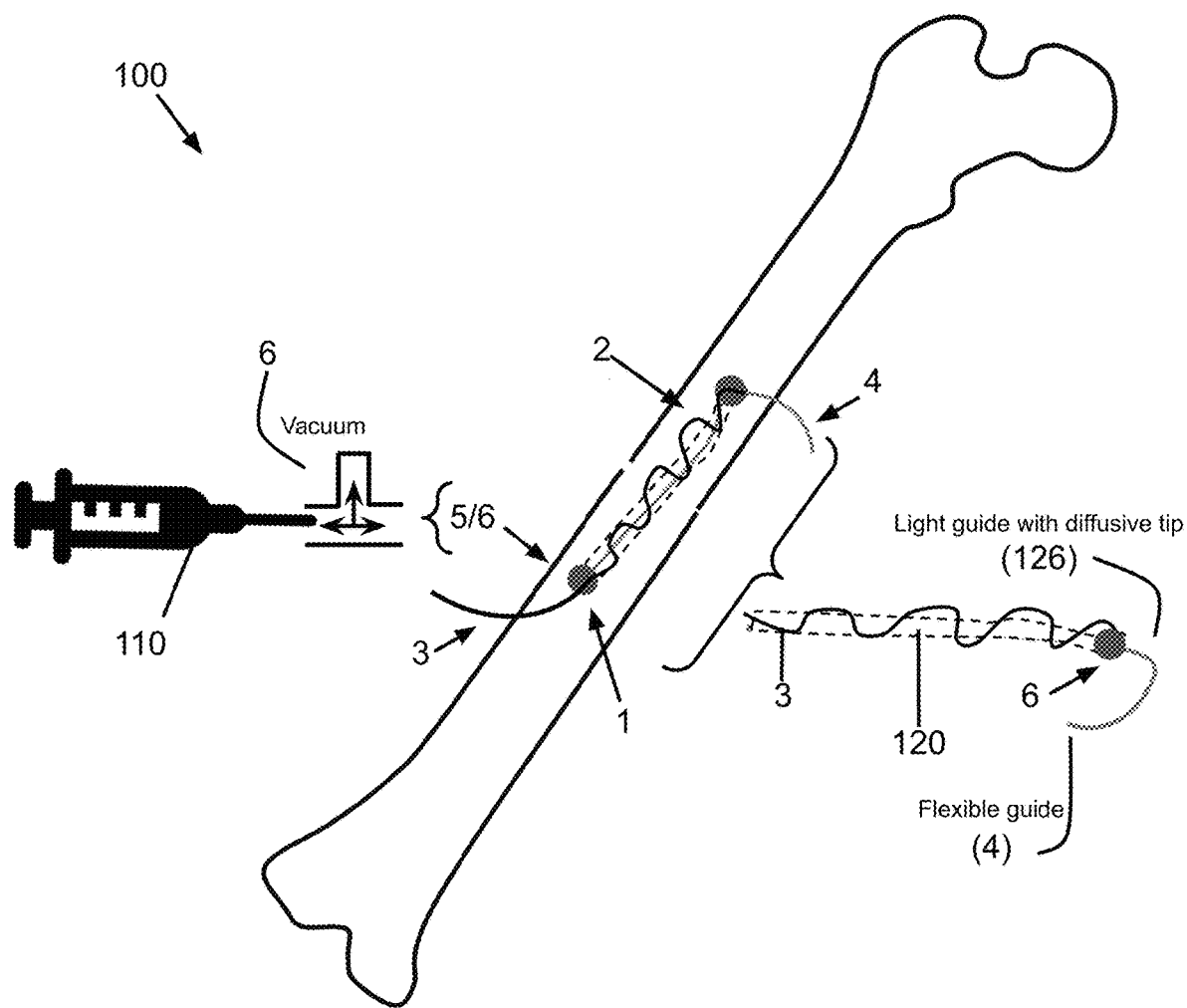
Figure 1C:
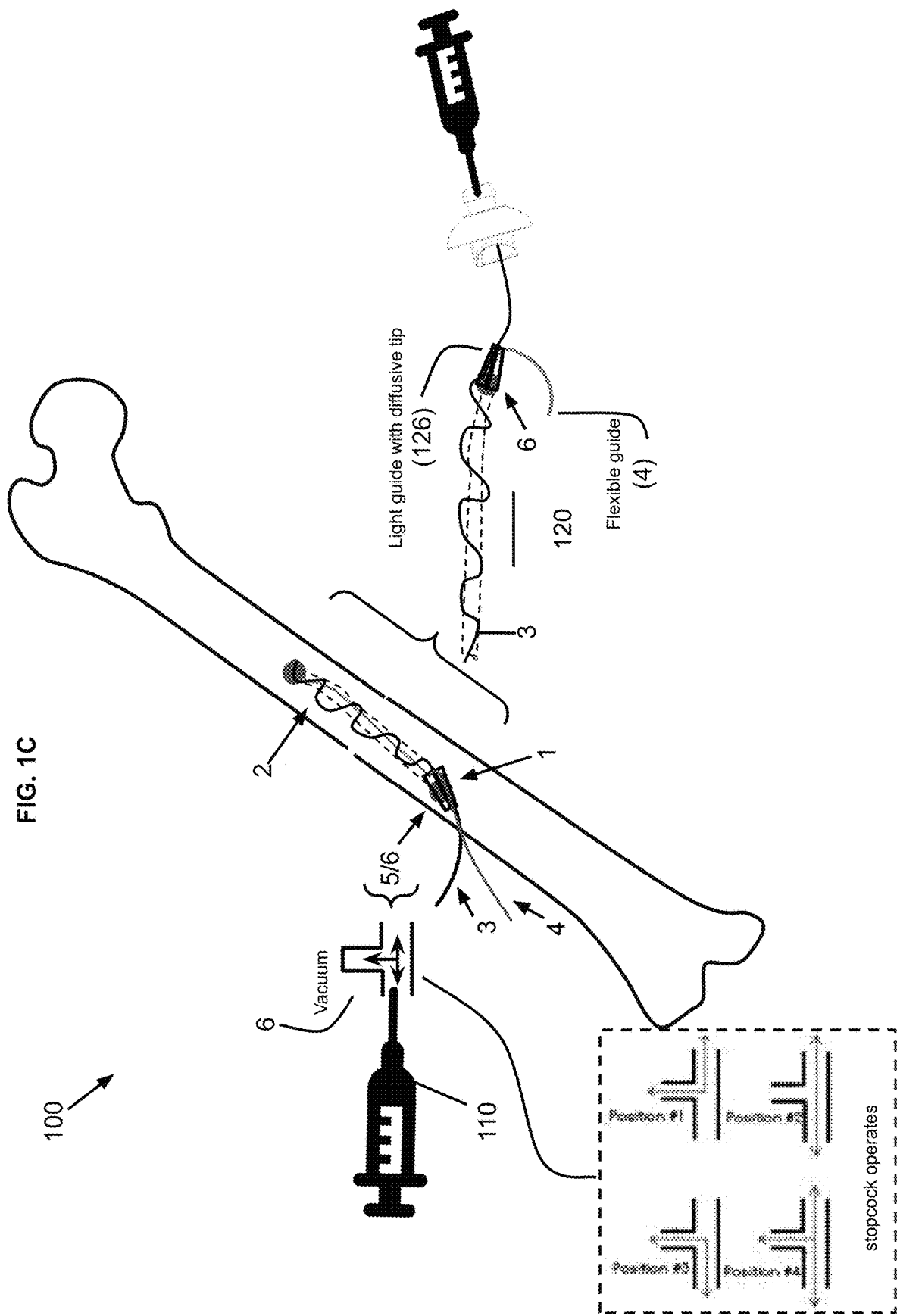
Figure 1D:
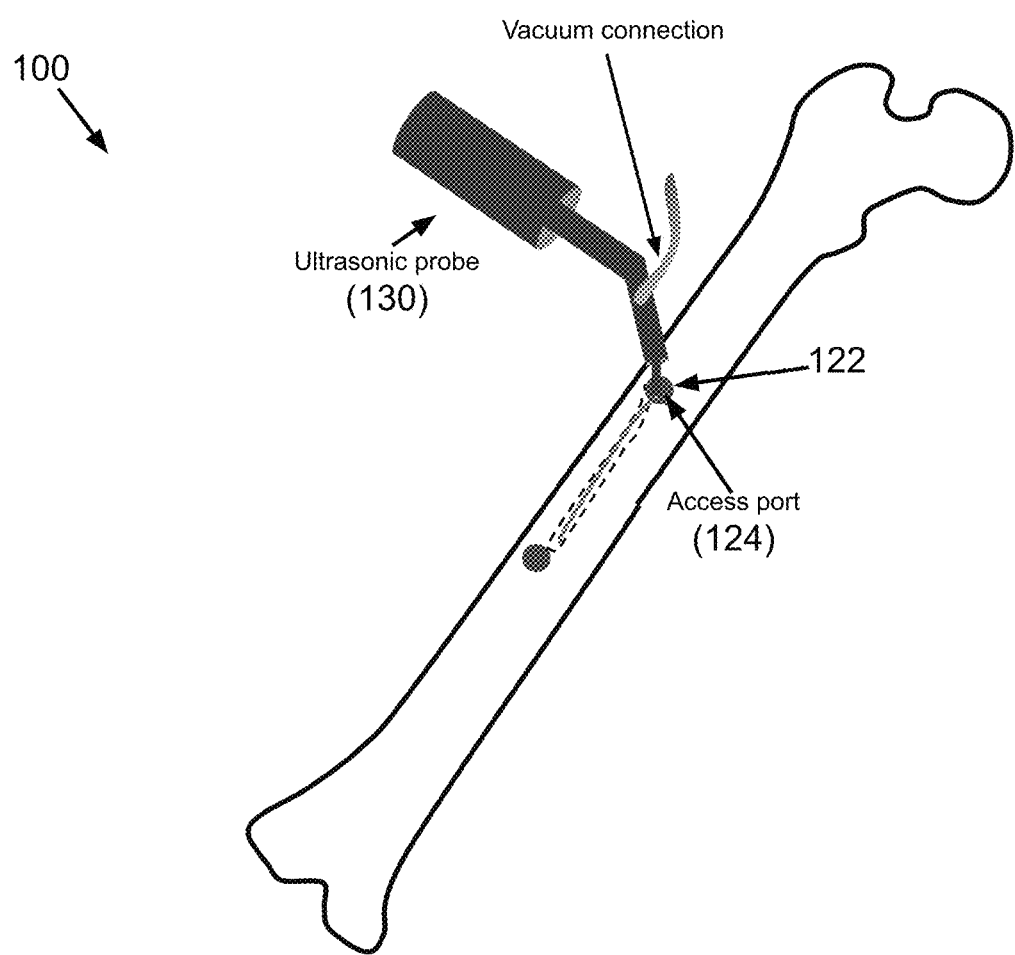
Figure 2A:
FIG. 2A shows a straight hollow probe with a sharp and hollow edge with a screw rotation system which helps to penetrate the material.
Figure 2B:
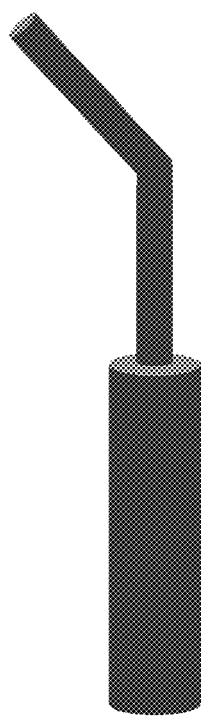
FIG. 2B shows a hollow probe that is bent to 60 degrees.
Figure 2C:
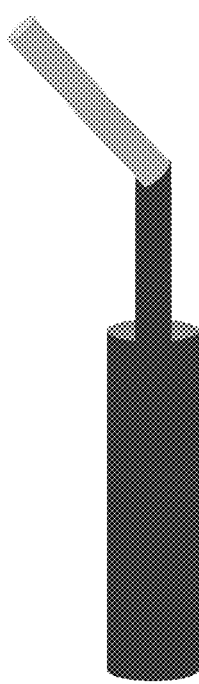
FIG. 2C shows a probe which has inner sharp edges.
Figure 2D:
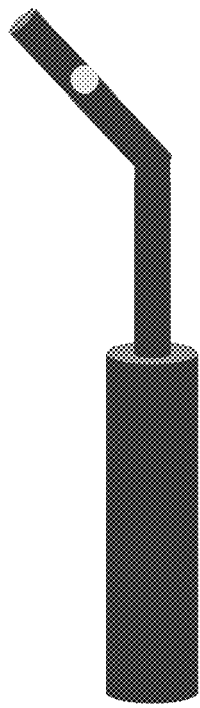
FIG. 2D shows a hollow probe bending region that has a 1 mm hole for pulling out removed material.
Figure 2E:
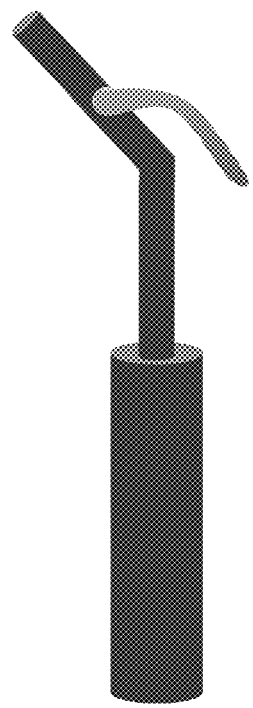
FIG. 2E shows a hollow bending probe that has an additional flexible tube for connecting vacuum suction.

FIGS. 1A, 1B, and 1C show an embodiment of a proximal end (1) of a flexible insertion multilayer layer sleeve (2) and a photocurable injection system (100) of the present disclosure for repairing a weakened or fractured bone. The intramedullary photocurable device includes a multilayer sleeve comprising an expandable portion (not visible in FIG. 1A) mounted at a distal end of the flexible insertion light guides (3, 4). In some embodiments, the intramedullary photocurable device comprises a flexible insertion sleeve. A proximal end access valve (5) includes at least one arm and one access valve that can be utilized for the infusion and withdrawal of polymeric resin. In some embodiments, an access valve is a duckbill valve. In some embodiments, an access valve is a multi-functional access valve. FIGS. 1A, 1B, and 1C show a side view of a single-arm proximal end-fitting access valve.

The access valve (6) can accept, for example, a syringe housing a photocurable polymeric resin (110) comprising functional materials. In some embodiments, the photosensitive liquid is a liquid-based resin mixture monomer and may comprise a photo-initiator, free-radical initiator, catalyst, additives, and a radiopaque material. The photoinitiator is activated when the light-guide fiber transmits light energy and initiates polymerization of the photocurable polymeric resin. In the traditional free-radical polymerization approach, the catalyst activates the free-radical initiator, producing radical species that, under mild conditions, promote radical reactions.

In some embodiments, a syringe housing the photocurable polymeric resin is attached to the access valve (6) at the proximal end (5) of the insertion sleeves (1). During the use of the system (100), the syringe plunger is pushed, allowing the syringe to expel the photocurable polymeric resin into an inner void (not visible in FIG. 1A) of the sleeve device as the photocurable polymeric resin (e.g., the photosensitive liquid material is expelled through the inner void of sleeves with expandable portions. The photosensitive liquid can be aspirated without reinfused, one injection is more than enough to achieve maximum fracture reduction before activating a light source and converting the liquid monomer into a hard solid polymer.

In some embodiments, a light guide fiber communicating light from a light source is introduced into the access valve (6) at the proximal end. In some embodiments, the light guide fiber is a light guide optical fiber. The present disclosure may use optical fibers to communicate light from the light source to a remote location. Optical fibers use the construction of concentric layers for optical and mechanical advantages. The most basic function of an optical fiber is to guide light, i.e., to keep light concentrated over longer propagation distances—despite the natural tendency of light beams to diverge, possibly even under conditions of strong bending. The extra light diffuser tip is connected near the cladding with different lengths (with requirements), which are made with similar functional chemistry to an intramedullary photocurable device system. The cladding is usually outside the sleeves and is protected with at least a polymer coating. Total internal reflection keeps light in the "core" of the optical fiber. In some embodiments of the present disclosure, at least a portion of a length of an optical fiber is modified, e.g., by removing the cladding, to alter the direction, propagation, amount, intensity, angle of incidence, uniformity, and/or distribution of light.

The photocurable polymeric resin remains a liquid material until activated by the light-guide fiber (e.g., cures on demand). Radiant energy from the light guide fiber is absorbed and converted to chemical energy to polymerize the monomer quickly. This cure affixes the sleeves with an expanded shape. A medication may refer to any chemical, physical, and mechanical transformation that allows a composition to progress from a form that will enable it to be delivered through the inner void in the insertion sleeves (1) into a more permanent (e.g., cured) form for final use in vivo. For example, "curable" may refer to an uncured composition having the potential to be cured in vivo (as by catalysis or the application of a suitable energy source), as well as to a composition in the process of curing (e.g., a composition formed at the time of delivery by the concurrent mixing of a plurality of composition components).

The present invention features a method for implementing in-situ polymerization via light to enable fractured bone fixation in a subject, comprising providing a photosensitive polymeric resin (110) sensitive to light, temperature, oxygen, enzymes, or a combination thereof. The photosensitive polymeric resin (110) may be configured to cure at room temperature or physiological temperature with a light source. The photosensitive polymeric resin or polymeric resin (110) may be curable with a free-radical method and may be configured to depolymerize at room temperature or physiological temperature or at a temperature lower than 40° C. with a free-radical catalyst, infrared light source, ultrasonication, sonication, or a combination thereof. The method may further comprise providing an implantable three-dimensional biocompatible sleeve (120) comprising one or more openings (122), one or more access ports (124) disposed at the one or more openings (122), and an optical light guide (126) disposed through the one or more access ports (124) comprising a light diffusive tip made from a biocompatible material. The method may further comprise providing one or more micro-sized ultrasonication probes (130) configured to contact a three-dimensional sleeve (120) by one or more openings (122). The one or more probes (130) may be configured to enable polymer outflow. The method may further comprise directing, through a drilled hole, the sleeve (120) into an interior of a bone, injecting the photosensitive polymeric resin through an access port of the one or more access ports, and actuating the optical light guide (126) such that the photosensitive polymeric resin (110) is cured in a shape of the interior of the bone.

The present invention features various embodiments of the removal/extraction approach of cured polymer with a minimally invasive process. In some embodiments, the removal system (e.g., the ultrasonic system) of the present disclosure is sufficiently designed to control the temperature. The present invention features methods for the removal of the cured bone cement/polymer from the sleeves inside the bone.

In some embodiments, the method for removing the photocured polymer comprising functional materials comprises actuating one or more micro-sized ultrasonic probes (130) configured to enter a three-dimensional sleeve (120)

by one or more openings (122). The one or more probes (130) may be configured to enable polymer outflow (e.g., via suction).

The removal/extraction process of the present invention is not limited to orthopedic implant removal and may also be used for dental implant removal or for the removal of any polymer-based implants.

In some embodiments, the method may further comprise providing one or more tools such as sensors and/or cameras. The one or more tools (e.g., sensors or cameras) may help to monitor the curing and removal process of the polymeric resin (110) and cured polymer, respectively. The sensors may be configured to detect pressure while the resin (110) is injected and/or when the cured polymer is removed. The cameras may be configured to visualize the injection and removal/extraction of the resin (110)/polymer.

The methods described herein may not use soluble or absorbable material and may help to resist infection. In some embodiments, the method comprises inserting multilayer sleeves into the bone cavity and injecting a biocompatible photocurable polymer resin. In this way, a solid peg is created inside the bone cavity that joins the sides of the fracture. The systems and methods described herein eliminate the need for open cuts and significantly reduce trauma and recovery time. In addition, the lack of metal eliminates potential interference problems with imaging techniques such as magnetic resonance imaging. The methods described in this disclosure provide a non-absorbable solution for repairing and strengthening bones that can be left in place permanently or removed if desired.

For example, in some embodiments, provided herein is a method of treating or stabilizing (e.g., by strengthening a bone) a bone fracture or supporting a bone in a subject, comprising the following: a) a low-density liquid resin (e.g., a photocurable polymeric resin comprising functional materials and a photoinitiator), where minimum pressure is used to inject the resin, and b) at least one hole (e.g., on the mm scale in diameter) through a bone, the hole having orthopedic duckbill valves (which can carry multilayer sleeves and a light guide), and optionally, c) filling the apparatus with a biocompatible polymer. In some embodiments, the holes are drilled (e.g., laparoscopy). In some embodiments, the fiber sleeves are removable (e.g., by activating a depolymerization/deplasticizing agent).

In some embodiments, the method herein may further comprise implementing a machine learning artificial intelligence (AI) algorithm based on a plurality of factors selected from a group comprising patient ages, bone density, region of fracture, and classification of fractures AI to identify optimal formulation and curing of polymeric resin. The AI algorithm may be trained by prior data mapping the plurality of factors to different formulations and curing techniques of the resin.

Example

The following is a non-limiting example of the present invention. It is to be understood that said example is not intended to limit the present invention in any way. Equivalents or substitutes are within the scope of the present invention.

Pediatric fracture: A 8-year-old patient with severe arm pain who could not move his arm or elbow arrived at the hospital. A pediatric orthopedic surgeon performs an X-ray evaluation and identifies the fracture in the proximal ulna. The surgeon strongly recommends using a photocurable injection system comprising an intramedullary sleeve device and a photocurable polymeric resin comprising function materials to treat the fractured ulna. The surgical procedure involves injecting the resin into the sleeve and ulna. Then curing the resin using the UV-Visible light device provided in a kit. The child recovers from the surgery in a day, and the fracture heals within two weeks. Finally, a surgeon performs a follow-up evaluation and recommends removing the cured resin after complete healing.

Young adult bone fracture: A 19-year-old girl fell on her arm on slippery ice and arrives at the hospital with extreme pain in her right arm. The doctor performs a humerus X-ray of external rotation AP and identifies the fracture in the surgical neck of the humerus. After observing the X-ray surgeon refers her to the orthopedic surgeon and recommends treatments with a minimally invasive photocurable polymeric resin comprising functional materials. The surgeon performs the surgery by inserting the IM sleeve device system into the patient's humerus bone, injecting a curable polymeric resin into the sleeve, and curing resin using a UV-Visible light guide. The patient recovers within two days. During the follow-up examination, the surgeon recommended removing the cured resin after complete healing.

Adult female phalanx fracture: A 35-year-old woman comes in with pain in the third finger of her left hand and is unable to lift her finger. The surgeon performs PA oblique X-ray and identifies a middle phalanx fracture. The surgeon performs surgery using intramedullary sleeves with one layer and photocurable polymeric resin comprising functional materials and smart nanomaterials—placed into the sleeve. The patient was discharged from the hospital the same day. The fracture heals after two weeks. During the follow-up visit, the surgeon arranges another simple surgery to remove the implant.

Geriatric fracture: A 65-year-old female patient with underlying conditions suffers a proximal trochanter fracture and visits the hospital. The surgeon performs X-ray screening, identifies the fracture type, and recommends that a minimally invasive fracture treatment comprising a photocurable injection system (100) be used for treatment of the fracture. The surgical procedure is performed by injecting the resin into the inserted sleeve system and curing the resin using the UV/visible light setup provided in the kit. The patient recovers within two days, and the fracture heals within four weeks. The surgeon performs a follow-up screening and recommends retaining the implant considering her age and risk for removal/extraction procedure as there is no noticeable infection.

Pathological fracture: 85 years old gentleman with severe osteoporosis fell down the stairs. An ambulance took him to the hospital. He was not able to move, and his foot hurt a lot. ER specialists perform a mediolateral femur x-ray. The doctor identifies a fracture in the midshaft of the femur. The orthopedic surgeon efficiently performs surgery using a wide two-layer sleeve and injecting a free-radical curable polymeric resin into the two-layer sleeve. However, because of age complications, the patient is required to stay in the hospital for one week. After a week, he has healed, and the surgeon recommends keeping the sleeve implanted and not opting for a removal surgery, considering the age factor.

EMBODIMENTS

The following embodiments are intended to be illustrative only and not to be limiting in any way.

Embodiment 1: A photocurable injection system (100) for creating in-situ polymerization of a photocurable polymeric resin to enable fractured bone fixation and extraction of a cured polymer, comprising: a) a high stiffness photocurable polymeric resin (110) comprising functional materials that are adapted to photocure into the cured polymer, wherein the cured polymer is pulverizable, b) a diffusive light guide tip; and c) a minimally invasive ultrasonic system for extracting the cured polymer; wherein the ultrasonic system is configured to pulverize the cured polymer into particles and wherein the ultrasonic system is configured to extract the particles.

Embodiment 2: The system (100) of embodiment 1, wherein the functional materials act as monomers, comonomers, short-chain crosslinkers, and long-chain crosslinkers or a combination thereof.

Embodiment 3: The system (100) of embodiment 1, wherein the photocurable polymeric resin (110) is activated by a photoinitiator.

Embodiment 4: The system (100) of embodiment 3, wherein the photoinitiator comprises diphenyl(2,4,6-trimethylbenzoyl)phosphine oxide, phenylbis(2,4,6-trimethylbenzoyl)phosphine oxide, 2-Hydroxy-4'-(2-hydroxyethoxy)-2-methylpropiophenone, or a combination thereof.

Embodiment 5: The system (100) of embodiment 1, wherein the functional materials comprise low melting point polymers modified with acrylate or methacrylate functional groups, a thermoplastic polymer with acrylate or methacrylate functional, semicrystalline polymers, unsaturated fatty acids modified with acrylate or methacrylate functional groups, modified acrylate or methacrylate functional groups of polypeptides, dendrimers, natural polysaccharide-based units, materials that can crosslink or act as a comonomers or monomer with a functional materials polymeric resin, or a combination thereof.

Embodiment 6: The system (100) of embodiment 1, wherein the functional materials comprise polymethylmethacrylate (PMMA) resin solution, isobornyl methacrylate, diurethane dimethacrylate, ethylene glycol dimethacrylate, polycaprolactone dimethacrylate, 1-Phenyl-2-propen-1-one, trimethylolpropane triacrylate, Pentaerythritol tetraacrylate, glycerol propoxylate (1PO/OH), tris[2-(acryloyloxy)ethyl] isocyanurate, triacrylatepentaerythritol tetraacrylate, dipentaerythritol penta-/hexa-acrylate, trimethylolpropane trimethacrylate, triethylene glycol dimethacrylate or a combination thereof.

Embodiment 7: The system (100) of embodiment 6, wherein the functional materials further comprise butyl acrylate, methacrylic acid, n-decyl methacrylate, 3,3,5-Trimethylcyclohexyl methacrylate, n-propyl methacrylate, n-propyl acrylate, benzyl methacrylate, N-butyl-methacrylate, n-octyl methacrylate, phenyl methacrylate, iso-Decyl acrylate, n-hexyl acrylate, sec-butyl methacrylate, iso-butyl methacrylate, cyclohexyl methacrylate, 2-phenoxyethyl methacrylate, sec-butyl acrylate, 2-methoxyethyl acrylate, ethyl methacrylate, 2-hydroxyethyl methacrylate, 2-ethylhexyl methacrylate, polyimide, ethylene glycol-based dimethacrylates, 2-n-butoxyethyl methacrylate, 2-[4'-iodobenzoyloxy]ethyl methacrylate, 2-[2',3',5'-triiodobenzoyloxy] ethyl methacrylate, or a combination thereof.

Embodiment 8: The system (100) of embodiment 6, wherein the diurethane dimethacrylate, the ethylene glycol dimethacrylate, and polycaprolactone dimethacrylate allow the cured polymer to be pulverizable.

Embodiment 9: The system (100) of embodiment 6, wherein the functional materials comprise about 10-98% W/W or V/V of the PMMA resin solution, about 0.5-50% W/W or V/V of isobornyl methacrylate, about 0.5-50% W/W or V/V of diurethane dimethacrylate, about 0.1-10% W/W or V/V of ethylene glycol dimethacrylate, about 0.1-10% W/W or V/V of polycaprolactone dimethacrylate, and about 0.1-10% W/W or V/V of Diphenyl(2, 4, 6-trimethylbenzoyl) phosphine oxide.

Embodiment 10: The system (100) of embodiment 6, wherein the functional materials comprise about 75-80% W/W or V/V of the PMMA resin solution, about 5-15% W/W or V/V of isobornyl methacrylate, about 1-10% W/W or V/V of diurethane dimethacrylate, about 0.1-5% W/W or V/V of ethylene glycol dimethacrylate, about 0.1-5% W/W or V/V of polycaprolactone dimethacrylate, and about 0.1-2% W/W or V/V of Diphenyl(2, 4, 6-trimethylbenzoyl) phosphine oxide.

Embodiment 11: The system (100) of embodiment 1, wherein the ultrasonic system is configured to extract particles through a laparoscopic opening.

Embodiment 12: A photocurable injection system (100) for creating in-situ polymerization of a photocurable polymeric resin to enable fractured bone fixation and extraction of a cured polymer, comprising: a) a high stiffness photocurable polymeric resin (110) comprising functional materials that are adapted to photocure into the cured polymer at a reaction temperature of at most 55 to 65° C.; b) a diffusive light guide tip; and c) a minimally invasive ultrasonic system for extraction of the cured polymer.

Embodiment 13: The system (100) of embodiment 12, further comprising a sleeve.

Embodiment 14: The system (100) of embodiment 13, wherein the photocurable polymeric resin (110) is photocured into the polymer inside the sleeve.

Embodiment 15: The system (100) of embodiment 14, wherein when photocuring the polymeric resin (110) into the polymer inside the sleeve, a temperature outside the sleeve is at most 40° C.

Embodiment 16: The system (100) of embodiment 12, wherein the functional materials act as a monomer, comonomers, a short-chain cross-linker, long chain crosslinker, or a combination thereof.

Embodiment 17: The system (100) of embodiment 12, wherein the photocurable polymeric resin (110) is activated by a photoinitiator.

Embodiment 18: The system (100) of embodiment 17, wherein the photoinitiator comprises diphenyl(2,4,6-trimethylbenzoyl)phosphine oxide, phenylbis(2,4,6-trimethylbenzoyl)phosphine oxide, 2-Hydroxy-4'-(2-hydroxyethoxy)-2-methylpropiophenone, or a combination thereof.

Embodiment 19: The system (100) of embodiment 12, wherein the functional materials comprise low melting point polymers modified with acrylate or methacrylate functional groups, a thermoplastic polymer with acrylate or methacrylate functional, semicrystalline polymers, unsaturated fatty acids modified with acrylate or methacrylate functional groups, modified acrylate or methacrylate functional groups of polypeptides, dendrimers, natural polysaccharide-based units, materials that can crosslink or act as a comonomers or monomer with a functional materials polymeric resin, or a combination thereof.

Embodiment 20: The system (100) of embodiment 12, wherein the functional materials comprise a polymethylmethacrylate (PMMA) resin solution, isobornyl methacrylate, diurethane dimethacrylate, ethylene glycol dimethacrylate, polycaprolactone dimethacrylate, or a combination thereof.

Embodiment 21: The system (100) of embodiment 20, wherein the functional materials further comprise butyl acrylate, methacrylic acid, n-decyl methacrylate, 3,3,5-Trimethylcyclohexyl methacrylate, n-propyl methacrylate, n-propyl acrylate, benzyl methacrylate, N-butyl-methacrylate, n-octyl methacrylate, phenyl methacrylate, iso-Decyl acrylate, n-hexyl acrylate, sec-butyl methacrylate, iso-butyl methacrylate, cyclohexyl methacrylate, 2-phenoxyethyl methacrylate, sec-butyl acrylate, 2-methoxyethyl acrylate, ethyl methacrylate, 2-hydroxyethyl methacrylate, 2-ethylhexyl methacrylate, ethylene glycol-based dimethacrylates, 2-n-butoxyethyl methacrylate, or a combination thereof.

Embodiment 22: The system (100) of embodiment 20, wherein the functional materials comprise about 10-98% W/W or V/V of the PMMA resin solution, about 0.5-50% W/W or V/V of isobornyl methacrylate, about 0.5-50% W/W or V/V of diurethane dimethacrylate, about 0.1-10% W/W or V/V of ethylene glycol dimethacrylate, about 0.1-10% W/W or V/V of polycaprolactone dimethacrylate, and about 0.1-10% W/W or V/V of Diphenyl(2, 4, 6-trimethylbenzoyl) phosphine oxide.

Embodiment 23: The system (100) of embodiment 20, wherein the functional materials comprise about 75-80% W/W or V/V of the PMMA resin solution, about 5-15% W/W or V/V of isobornyl methacrylate, about 1-10% W/W or V/V of diurethane dimethacrylate, about 0.1-5% W/W or V/V of ethylene glycol dimethacrylate, about 0.1-5% W/W or V/V of polycaprolactone dimethacrylate, and about 0.1-2% W/W or V/V of Diphenyl(2, 4, 6-trimethylbenzoyl) phosphine oxide.

Embodiment 24: The system (100) of embodiment 12, wherein the ultrasonic system is configured to extract the cured polymer through a laparoscopic opening.

Embodiment 25: A photocurable injection system (100) for creating in-situ polymerization of a photocurable polymeric resin to enable fractured bone fixation and extraction of a cured polymer, comprising: a) a high stiffness photocurable polymeric resin (110) comprising functional materials that are adapted to photocure into the polymer, wherein the cured polymer shrinks in volume by less than 2% as compared to the original volume of the uncured polymer; b) a diffusive light guide tip; and c) a minimally invasive ultrasonic system for extraction of the cured polymer.

Embodiment 26: The system (100) of embodiment 25, wherein the functional materials act as a monomer, comonomers, a short-chain cross-linker, and long chain-crosslinker.

Embodiment 27: The system (100) of embodiment 25, wherein the photocurable polymeric resin (110) is activated by a photoinitiator.

Embodiment 28: The system (100) of embodiment 27, wherein the photoinitiator comprises diphenyl(2,4,6-trimethylbenzoyl)phosphine oxide, phenylbis(2,4,6-trimethylbenzoyl)phosphine oxide, 2-Hydroxy-4'-(2-hydroxyethoxy)-2-methylpropiophenone, or a combination thereof.

Embodiment 29: The system (100) of embodiment 25, wherein the functional materials comprise low melting point polymers modified with acrylate or methacrylate functional groups, a thermoplastic polymer with acrylate or methacrylate functional, semicrystalline polymers, unsaturated fatty acids modified with acrylate or methacrylate functional groups, modified acrylate or methacrylate functional groups of polypeptides, dendrimers, natural polysaccharide-based units, materials that can crosslink or act as a comonomers or monomer with a functional materials polymeric resin, or a combination thereof.

Embodiment 30: The system (100) of embodiment 25, wherein the functional materials comprise a polymethylmethacrylate (PMMA) resin solution, isobornyl methacrylate, diurethane dimethacrylate, ethylene glycol dimethacrylate, polycaprolactone dimethacrylate, or a combination thereof.

Embodiment 31: The system (100) of embodiment 30, wherein the functional materials further comprise butyl acrylate, methacrylic acid, n-decyl methacrylate, 3,3,5-Trimethylcyclohexyl methacrylate, n-propyl methacrylate, n-propyl acrylate, benzyl methacrylate, N-butyl-methacrylate, n-octyl methacrylate, phenyl methacrylate, iso-Decyl acrylate, n-hexyl acrylate, sec-butyl methacrylate, iso-butyl methacrylate, cyclohexyl methacrylate, 2-phenoxyethyl methacrylate, sec-butyl acrylate, 2-methoxyethyl acrylate, ethyl methacrylate, 2-hydroxyethyl methacrylate, 2-ethylhexyl methacrylate, ethylene glycol-based dimethacrylates, 2-n-butoxyethyl methacrylate, or a combination thereof.

Embodiment 32: The system (100) of embodiment 30, wherein the PMMA resin solution, the isobornyl methacrylate, the diurethane dimethacrylate, the ethylene glycol dimethacrylate, and the polycaprolactone dimethacrylate allows the cured polymer to shrink in volume by less than 2% as compared to the original volume of the uncured polymer.

Embodiment 33: The system (100) of embodiment 30, wherein the functional materials comprise about 10-98% W/W or V/V of the PMMA resin solution, about 0.5-50% W/W or V/V of isobornyl methacrylate, about 0.5-50% W/W or V/V of diurethane dimethacrylate, about 0.1-10% W/W or V/V of ethylene glycol dimethacrylate, about 0.1-10% W/W or V/V of polycaprolactone dimethacrylate, and about 0.1-10% W/W or V/V of Diphenyl(2, 4, 6-trimethylbenzoyl) phosphine oxide.

Embodiment 34: The system (100) of embodiment 30, wherein the functional materials comprise about 75-80% W/W or V/V of the PMMA resin solution, about 5-15% W/W or V/V of isobornyl methacrylate, about 1-10% W/W or V/V of diurethane dimethacrylate, about 0.1-5% W/W or V/V of ethylene glycol dimethacrylate, about 0.1-5% W/W or V/V of polycaprolactone dimethacrylate, and about 0.1-2% W/W or V/V of Diphenyl(2, 4, 6-trimethylbenzoyl) phosphine oxide.

Embodiment 35: The system (100) of embodiment 25, wherein the ultrasonic system is configured to extract the cured polymer through a laparoscopic opening.

Embodiment 36: A method for repairing a bone fracture, the method comprising: a) injecting a high stiffness photocurable polymeric resin (110) into a medullary cavity of a fractured bone, wherein the photocurable polymeric resin (110) comprises functional materials that are adapted to photocure into the polymer, and wherein the cured polymer is pulverizable; b) photopolymerizing the photocurable polymeric resin (110) in-situ using a diffusive light guide tip to produce a cured polymer, wherein a reaction temperature is at most 55 to 65° C., wherein the cured polymer shrinks in volume by less than 2% as compared to the original volume of the uncured polymer; c) pulverizing the cured polymer into particles using a minimally invasive ultrasonic system; and d) extracting the particles.

Embodiment 37: The method of embodiment 36, further comprising injecting the photocurable polymeric resin (110) into a sleeve in the medullary cavity of the fractured bone.

Embodiment 38: The method of embodiment 37, wherein the photocurable polymeric resin (110) is photocured into the polymer inside the sleeve.

Embodiment 39: The method of embodiment 38, wherein when curing the photocurable polymeric resin (110) into the polymer inside the sleeve, a temperature outside the sleeve is at most 40° C.

Embodiment 40: The method of embodiment 36, wherein the functional materials act as a monomer, comonomers, short-chain cross-linker, and long chain-crosslinker.

Embodiment 41: The method of embodiment 36, wherein the photocurable polymeric resin (110) is activated by a photoinitiator, a free radical initiator, or a combination thereof.

Embodiment 42: The method of embodiment 41, wherein the photoinitiator comprises diphenyl(2,4,6-trimethylbenzoyl)phosphine oxide, phenylbis(2,4,6-trimethylbenzoyl) phosphine oxide, 2-Hydroxy-4'-(2-hydroxyethoxy)-2-methylpropiophenone, or a combination thereof.

Embodiment 43: The method of embodiment 36, wherein the functional materials comprise low melting point polymers modified with acrylate or methacrylate functional groups, a thermoplastic polymer with acrylate or methacrylate functional, semicrystalline polymers, unsaturated fatty acids modified with acrylate or methacrylate functional groups, modified acrylate or methacrylate functional groups of polypeptides, dendrimers, natural polysaccharide-based units, materials that can crosslink or act as a comonomers or monomer with a functional materials polymeric resin, or a combination thereof.

Embodiment 44: The method of embodiment 36 wherein the functional materials comprise a polymethylmethacrylate (PMMA) resin solution, isobornyl methacrylate, diurethane dimethacrylate, ethylene glycol dimethacrylate, triethylene glycol dimethacrylate, polycaprolactone dimethacrylate, or a combination thereof.

Embodiment 45: The method of embodiment 44, wherein the functional materials further comprise butyl acrylate, methacrylic acid, n-decyl methacrylate, 3,3,5-Trimethylcyclohexyl methacrylate, n-propyl methacrylate, n-propyl acrylate, benzyl methacrylate, N-butyl-methacrylate, n-octyl methacrylate, phenyl methacrylate, iso-Decyl acrylate, n-hexyl acrylate, sec-butyl methacrylate, iso-butyl methacrylate, cyclohexyl methacrylate, 2-phenoxyethyl methacrylate, sec-butyl acrylate, 2-methoxyethyl acrylate, ethyl methacrylate, 2-hydroxyethyl methacrylate, polyimide, 2-ethylhexyl methacrylate, ethylene glycol-based dimethacrylates, 2-n-butoxyethyl methacrylate, or a combination thereof.

Embodiment 46: The method of embodiment 44, wherein the functional materials comprise about 75-80% W/W or V/V of the PMMA resin solution, about 5-15% W/W or V/V of isobornyl methacrylate, about 1-10% W/W or V/V of diurethane dimethacrylate, about 0.1-5% W/W or V/V of ethylene glycol dimethacrylate, about 0.1-5% W/W or V/V of polycaprolactone dimethacrylate, and about 0.1-2% W/W or V/V of Diphenyl(2, 4, 6-trimethylbenzoyl) phosphine oxide.

Embodiment 47: The method of embodiment 44, wherein the functional materials comprise about 75-80% W/W or V/V of the PMMA resin solution, about 5-15% W/W or V/V of isobornyl methacrylate, about 1-10% W/W or V/V of diurethane dimethacrylate, about 0.1-5% W/W or V/V of ethylene glycol dimethacrylate, about 0.1-5% W/W or V/V of polycaprolactone dimethacrylate, and about 0.1-2% W/W or V/V of Diphenyl(2, 4, 6-trimethylbenzoyl) phosphine oxide.

Embodiment 48: The method of embodiment 36, wherein the ultrasonic system is configured to extract the particles through a laparoscopic opening.

Embodiment 49: A method for repairing a bone fracture, the method comprising: a) injecting a high stiffness photocurable polymeric resin (110) into a medullary cavity of the fractured bone, wherein the photocurable polymeric resin (110) comprises functional materials that are adapted to photocure into a cured polymer, wherein the functional materials comprise: i) about 50-80% W/W or V/V of a resin solution, ii) about 1-50% W/W or V/V of a comonomer, iii) about 0.1-20% W/W or V/V of one or more short chain crosslinkers, iv) about 0.1-40% W/W or V/V of one or more long-chain crosslinkers, and v) about 0.1-5% W/W or V/V of a photoinitiator; b) photopolymerizing the photocurable polymeric resin (110) in-situ using a diffusive light guide tip to produce the cured polymer, wherein the cured polymer is pulverizable, wherein a reaction temperature is at most 55 to 65° C., wherein the cured polymer shrinks in volume by less than 2% as compared to the original volume of the uncured polymer; c) pulverizing the cured polymer into particles using a minimally invasive ultrasonic system; and d) extracting the particles.

Embodiment 50: The method of embodiment 49, wherein the photocurable polymeric resin (110) is injected into a sleeve that is inserted into the medullary cavity.

Embodiment 51: The method of embodiment 50, wherein the photocurable polymeric resin (110) is photocured inside the sleeve.

Embodiment 52: The method of embodiment 51, wherein when curing the photocurable polymeric resin (110) inside the sleeve, a temperature outside the sleeve is at most 40° C.

Embodiment 53: The method of embodiment 49, wherein the functional materials comprise a polymethylmethacrylate (PMMA) resin solution, isobornyl methacrylate, diurethane dimethacrylate, ethylene glycol dimethacrylate, polycaprolactone dimethacrylate, 1-Phenyl-2-propen-1-one, trimethylolpropane triacrylate, Pentaerythritol tetraacrylate, glycerol propoxylate (1PO/OH), tris[2-(acryloyloxy)ethyl] isocyanurate, triacrylatepentaerythritol tetraacrylate, dipentaerythritol penta-/hexa-acrylate, trimethylolpropane trimethacrylate, triethylene glycol dimethacrylate or a combination thereof.

Embodiment 54: The method of embodiment 53, wherein the functional materials further comprise butyl acrylate, methacrylic acid, n-decyl methacrylate, 3,3,5-Trimethylcyclohexyl methacrylate, n-propyl methacrylate, n-propyl acrylate, benzyl methacrylate, N-butyl-methacrylate, n-octyl methacrylate, phenyl methacrylate, iso-Decyl acrylate, n-hexyl acrylate, sec-butyl methacrylate, iso-butyl methacrylate, cyclohexyl methacrylate, 2-phenoxyethyl methacrylate, sec-butyl acrylate, 2-methoxyethyl acrylate, ethyl methacrylate, Poly($\alpha$-methylstyrene), 2-hydroxyethyl methacrylate, 2-ethylhexyl methacrylate, ethylene glycol-based dimethacrylates, 2-n-butoxyethyl methacrylate, 2-[4'-iodobenzoyloxy]ethyl methacrylate, 2-[2',3',5'-triiodobenzoyloxy]ethyl methacrylate or a combination thereof.

Embodiment 55: The method of embodiment 49, wherein the resin solution comprises a polymethylmethacrylate (PMMA) resin solution, a polystyrene (PS) resin solution, or a styrene resin solution and in-organic or organic radiopacity materials or a combination thereof.

Embodiment 56: The method of embodiment 49, wherein the photoinitiator comprises 2-Hydroxy-4'-(2-hydroxyethoxy)-2-methylpropiophenone, diphenyl(2,4,6-trimethylbenzoyl)phosphine oxide, phenylbis(2,4,6-trimethylbenzoyl)phosphine oxide, 4,4'-Bis(diethylamino) benzophenone, 2-Benzyl-2-(dimethylamino)-4'morpholinobutyrophenone, 4,4'-Bis(dimethylamino) benzophenone2-Chlorothioxanthen-9-one, 4-(Dimethylamino)benzophenone, 3'-Hydroxyacetophenone, methybenzoylformate, phenanthrenequinone, thioxanthen-9-one, camphorquinone, 2,2'-Azobis(2-methylpropionitrile),2-Hydroxy-4'-(2-hydroxyethoxy)-2-methylpropiophenone, or a combination thereof.

Embodiment 57: The method of embodiment 49, wherein the particles are extracted through a laparoscopic opening.

Embodiment 58: A photocurable injection system (100) for repairing a bone fracture, comprising: a) a photocurable polymeric resin (110) comprising functional materials that are adapted to photocure into a stiff cured polymer that is pulverizable, wherein the functional materials comprise: i) about 50-80% W/W or V/V of a resin solution, ii) about 1-50% W/W or V/V of a comonomer, iii) about 0.1-20% W/W or V/V of one or more short chain crosslinkers, iv) about 0.1-40% W/W or V/V of one or more long-chain crosslinkers, and v) about 0.1-5% W/W or V/V of a photoinitiator; b) a diffusive light guide tip for photopolymerizing the photocurable polymeric resin (110) in-situ; and c) a minimally invasive ultrasonic system for extracting the cured polymer, wherein the ultrasonic system is configured to pulverize the cured polymer into particles and extract said particles.

Embodiment 59: A stiff biocompatible polymer produced by curing a photocurable composition comprising: a) a photocurable polymeric resin (110); b) functional materials, wherein the functional materials comprise a monomer, one or more comonomers, a short chain cross-linker, and a long-chain crosslinker, or a combination thereof; and c) a photoinitiator; wherein the functional materials are adapted to photocure the reactive mixture into the stiff polymer composition.

Embodiment 60: A stiff biocompatible polymer produced by curing a photocurable composition comprising: a) about 50% to 80% W/W or V/V of a polymeric resin (110); b) about 1% to 50% W/W or V/V of a comonomer; c) about 0.1% to 20% W/W or V/V of one or more short chain crosslinkers; d) about 0.1% to 40% W/W or V/V of one or more long-chain crosslinkers; and e) about 0.1-5% W/W or V/V a photoinitiator.

Embodiment 61: A stiff biocompatible polymer produced by curing a photocurable composition comprising: a) about 75% to 80% W/W or V/V of a polymeric resin (110); b) about 15% to 10% W/W or V/V of isobornyl methacrylate; c) about 10% to 1% W/W or V/V of diurethane dimethacrylate; d) about 5% to 0.1% W/W or V/V of ethylene glycol dimethacrylate; e) about 5% to 0.1% W/W or V/V of polycaprolactone dimethacrylate; and f) about 0.1-2% W/W or V/V a photoinitiator.

As used herein, the term "about" refers to plus or minus 10% of the referenced number.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A photocurable injection system (100) for creating in-situ polymerization of a photocurable polymeric resin to enable fractured bone fixation and extraction of a cured polymer, comprising:
   a) a photocurable polymeric resin (110) comprising functional materials that are adapted to photocure into a stiff cured polymer that is pulverizable;
   b) a diffusive light guide tip; and
   c) a minimally invasive ultrasonic system for extracting the cured polymer;
   wherein the ultrasonic system is configured to pulverize the cured polymer into particles and extract said particles.

2. The system (100) of claim 1, wherein the functional materials act as a monomer, comonomers, a cross-linker, or combination thereof.

3. The system (100) of claim 1, wherein the photocurable polymeric resin (110) is activated by a photoinitiator.

4. The system (100) of claim 3, wherein the photoinitiator comprises 2-Hydroxy-4'-(2-hydroxyethoxy)-2-methylpropiophenone, diphenyl(2,4,6-trimethylbenzoyl)phosphine oxide, phenylbis(2,4,6-trimethylbenzoyl)phosphine oxide, or a combination thereof.

5. The system (100) of claim 1, wherein the functional materials comprise low melting point polymers modified with acrylate or methacrylate functional groups, thermoplastic polymers with acrylate or methacrylate functional, semicrystalline polymers, unsaturated fatty acids modified with acrylate or methacrylate functional groups, modified acrylate or methacrylate functional groups of polypeptides, dendrimers, natural polysaccharide-based units, materials that can crosslink or act as a comonomer or monomer with a functional materials polymeric resin, or a combination thereof.

6. The system (100) of claim 1, wherein the functional materials comprise a polymethylmethacrylate (PMMA) resin solution, isobornyl methacrylate, diurethane dimethacrylate, ethylene glycol dimethacrylate, polycaprolactone dimethacrylate, or a combination thereof.

7. The system (100) of claim 6, wherein the functional materials further comprise butyl acrylate, methacrylic acid, n-decyl methacrylate, 3,3,5-Trimethylcyclohexyl methacrylate, n-propyl methacrylate, n-propyl acrylate, benzyl methacrylate, N-butyl-methacrylate, n-octyl methacrylate, phenyl methacrylate, iso-Decyl acrylate, n-hexyl acrylate, sec-butyl methacrylate, iso-butyl methacrylate, cyclohexyl methacrylate, 2-phenoxyethyl methacrylate, sec-butyl acrylate, 2-methoxyethyl acrylate, ethyl methacrylate, 2-hydroxyethyl methacrylate, 2-ethylhexyl methacrylate, ethylene glycol-based dimethacrylates, 2-n-butoxyethyl methacrylate, or a combination thereof.

8. The system (100) of claim 6, wherein the functional materials comprise the diurethane dimethacrylate, the ethylene glycol dimethacrylate and the polycaprolactone dimethacrylate, wherein the diurethane dimethacrylate, the ethylene glycol dimethacrylate and the polycaprolactone dimethacrylate allow the cured polymer to be pulverizable.

9. The system (100) of claim 6, wherein the functional materials comprise about 75% to 80% W/W or V/V of the PMMA resin solution, about 15% to 10% W/W or V/V of isobornyl methacrylate, about 10% to 1% W/W or V/V of diurethane dimethacrylate, about 5% to 0.1% W/W or V/V of ethylene glycol dimethacrylate, and about 5% to 0.1% W/W or V/V of polycaprolactone dimethacrylate.

10. The system (100) of claim 6, wherein the functional materials comprise about 78.5% W/W or V/V of the PMMA resin solution, about 10% W/W or V/V of isobornyl methacrylate, about 5% W/W or V/V of diurethane dimethacrylate, about 3% W/W or V/V of ethylene glycol dimethacrylate, and about 3% W/W or V/V of polycaprolactone dimethacrylate.

11. The system (100) of claim 1, wherein the ultrasonic system is configured to extract particles through a laparoscopic opening.

12. A photocurable injection system (100) for creating in-situ polymerization of a photocurable polymeric resin to enable fractured bone fixation and extraction of a cured polymer, comprising:
   a) a photocurable polymeric resin (110) comprising functional materials that are adapted to photocure into a stiff cured polymer that is pulverizable; wherein the functional materials comprise:
      i) about 80% to 75% W/W or V/V of polymethylmethacrylate (PMMA) resin solution;
      ii) about 10% to 15% W/W or V/V of isobornyl methacrylate;
      iii) about 1% to 10% W/W or V/V of diurethane dimethacrylate;
      iv) about 0.1% to 5% W/W or V/V of ethylene glycol dimethacrylate, and
      v) about 0.1% to 5% W/W or V/V of polycaprolactone dimethacrylate;
   b) a diffusive light guide tip; and
   c) a minimally invasive ultrasonic system for extracting the cured polymer; wherein the ultrasonic system is configured to pulverize the cured polymer into particles and wherein the ultrasonic system is configured to extract the particles.

13. The system (100) of claim 12, wherein the photocurable polymeric resin (110) comprises about 0.1-2% W/W or V/V of a photoinitiator.

14. The system (100) of claim 13, wherein the photoinitiator comprises 2-Hydroxy-4'-(2-hydroxyethoxy)-2-methylpropiophenone, diphenyl(2,4,6-trimethylbenzoyl)phosphine oxide, phenylbis(2,4,6-trimethylbenzoyl)phosphine oxide, or a combination thereof.

15. The system (100) of claim 12, wherein the functional materials further comprise butyl acrylate, methacrylic acid, n-decyl methacrylate, 3,3,5-Trimethylcyclohexyl methacrylate, n-propyl methacrylate, n-propyl acrylate, benzyl methacrylate, N-butyl-methacrylate, n-octyl methacrylate, phenyl methacrylate, iso-Decyl acrylate, n-hexyl acrylate, sec-butyl methacrylate, iso-butyl methacrylate, cyclohexyl methacrylate, 2-phenoxyethyl methacrylate, sec-butyl acrylate, 2-methoxyethyl acrylate, ethyl methacrylate, 2-hydroxyethyl methacrylate, 2-ethylhexyl methacrylate, ethylene glycol-based dimethacrylates, 2-n-butoxyethyl methacrylate, or a combination thereof.

16. The system (100) of claim 12, wherein the functional materials comprise about 78.5% W/W or V/V of the PMMA resin solution, about 10% W/W or V/V of isobornyl methacrylate, about 5% W/W or V/V of diurethane dimethacrylate, about 3% W/W or V/V of ethylene glycol dimethacrylate, and about 3% W/W or V/V of polycaprolactone dimethacrylate.

17. The system (100) of claim 12, wherein the ultrasonic system is configured to extract particles through a laparoscopic opening.

18. A stiff biocompatible polymer produced by curing a photocurable composition comprising:
   a) about 75% to 80% W/W or V/V of a photocurable polymeric resin (110);
   b) about 5% to 15% W/W or V/V of isobornyl methacrylate;
   c) about 1% to 10% W/W or V/V of diurethane dimethacrylate;
   d) about 0.1% to 5% W/W or V/V of ethylene glycol dimethacrylate;
   e) about 0.1% to 5% W/W or V/V of polycaprolactone dimethacrylate; and
   f) about 0.1 to 2% W/W or V/V a photoinitiator.

19. The polymer of claim 18, wherein the photocurable polymeric resin (110) comprises a polymethylmethacrylate (PMMA) resin solution, a polystyrene (PS) resin solution, or a styrene resin solution.

20. The composition polymer of claim 19, wherein the photo initiator comprises 2-Hydroxy-4'-(2-hydroxyethoxy)-2-methylpropiophenone, diphenyl(2,4,6-trimethylbenzoyl)phosphine oxide, phenylbis(2,4,6-trimethylbenzoyl)phosphine oxide, or a combination thereof.

\* \* \* \* \*